(12) United States Patent
Laurence et al.

(10) Patent No.: US 11,413,159 B2
(45) Date of Patent: Aug. 16, 2022

(54) LATERAL INSERTION SPINAL IMPLANT

(71) Applicant: DePuy Synthes Products, Inc., Raynham, MA (US)

(72) Inventors: Lawton Laurence, West Chester, PA (US); Sean Saidha, Basel (CH); Michael White, Basel (CH); Khawar Mohammad Siddique, Los Angeles, CA (US); Brian Regis Perri, Los Angeles, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/954,321

(22) Filed: Apr. 16, 2018

(65) Prior Publication Data
US 2018/0303622 A1 Oct. 25, 2018

Related U.S. Application Data

(63) Continuation of application No. 13/932,771, filed on Jul. 1, 2013, now Pat. No. 9,943,417.
(Continued)

(51) Int. Cl.
*A61F 2/44* (2006.01)
*A61F 2/30* (2006.01)
(Continued)

(52) U.S. Cl.
CPC ............ *A61F 2/447* (2013.01); *A61F 2/4465* (2013.01); *A61F 2/4611* (2013.01); *A61B 17/863* (2013.01);
(Continued)

(58) Field of Classification Search
CPC .. A61F 2/44; A61F 2/445; A61F 2/447; A61F 2/4405–4495
See application file for complete search history.

(56) References Cited

U.S. PATENT DOCUMENTS

| 5,534,031 | A | 7/1996 | Matsuzaki et al. |
| 5,860,973 | A | 1/1999 | Michelson |

(Continued)

FOREIGN PATENT DOCUMENTS

| AU | 2004232317 | 11/2004 |
| AU | 2007342255 | 7/2008 |

(Continued)

OTHER PUBLICATIONS

Extended Search Report, dated Apr. 5, 2018, received in connection with corresponding EP Patent Application No. 18158754.4.
(Continued)

*Primary Examiner* — Tessa M Matthews
(74) *Attorney, Agent, or Firm* — Meunier Carlin & Curfman LLC

(57) ABSTRACT

The present disclosure relates to a spinal implant. The spinal implant may be used for lateral insertion into an intervertebral disc space. For example, the spinal implant may include a spacer body to which a plate is fixed. The intervertebral spacer body may include a pair of opposite sides having a pyramid-shaped teeth to fuse to bone. The plate defines at least one upper and lower borehole that each receives a screw. Each screw attaches the plate to a vertebral body between which the intervertebral spacer body is inserted. The boreholes may include locking threads that are adapted to lock the screws into place by engaging complementary locking threads of head of the screw.

20 Claims, 24 Drawing Sheets

Related U.S. Application Data

(60) Provisional application No. 61/666,335, filed on Jun. 29, 2012.

(51) Int. Cl.
*A61F 2/46* (2006.01)
*A61B 17/86* (2006.01)

(52) U.S. Cl.
CPC ......... *A61B 17/864* (2013.01); *A61B 17/8615* (2013.01); *A61F 2002/305* (2013.01); *A61F 2002/3008* (2013.01); *A61F 2002/30576* (2013.01); *A61F 2002/30578* (2013.01); *A61F 2002/30593* (2013.01); *A61F 2002/30607* (2013.01); *A61F 2002/30616* (2013.01); *A61F 2002/30785* (2013.01); *A61F 2002/30787* (2013.01); *A61F 2002/30843* (2013.01); *A61F 2310/00023* (2013.01); *A61F 2310/00095* (2013.01); *A61F 2310/00131* (2013.01)

(56) References Cited

U.S. PATENT DOCUMENTS

| | | | |
|---|---|---|---|
| 5,968,098 A | 10/1999 | Winslow | |
| 6,066,175 A * | 5/2000 | Henderson | A61F 2/44 623/17.11 |
| 6,106,557 A | 8/2000 | Robioneck et al. | |
| 6,120,503 A | 9/2000 | Michelson | |
| 6,136,001 A | 10/2000 | Michelson | |
| 6,156,037 A | 12/2000 | LeHuec et al. | |
| 6,296,647 B1 | 10/2001 | Robioneck et al. | |
| 6,342,074 B1 | 1/2002 | Simpson | |
| 6,364,880 B1 | 4/2002 | Michelson | |
| 6,432,106 B1 | 8/2002 | Fraser | |
| 6,447,545 B1 | 9/2002 | Bagby | |
| 6,716,245 B2 | 4/2004 | Pasquet et al. | |
| 6,726,722 B2 | 4/2004 | Walkenhorst et al. | |
| 6,805,714 B2 | 10/2004 | Sutcliffe | |
| 6,899,735 B2 | 5/2005 | Coates et al. | |
| 6,984,234 B2 | 1/2006 | Bray | |
| 7,041,135 B2 | 5/2006 | Michelson | |
| 7,112,222 B2 | 9/2006 | Fraser et al. | |
| 7,207,991 B2 | 4/2007 | Michelson | |
| 7,255,698 B2 | 8/2007 | Michelson | |
| 7,326,248 B2 | 2/2008 | Michelson | |
| 7,341,590 B2 | 3/2008 | Ferree | |
| 7,594,931 B2 | 9/2009 | Louis et al. | |
| 7,691,146 B2 | 4/2010 | Zucherman et al. | |
| 7,708,779 B2 | 5/2010 | Edie et al. | |
| 7,819,903 B2 | 10/2010 | Fraser et al. | |
| 7,887,595 B1 | 2/2011 | Pimenta | |
| 7,914,554 B2 | 3/2011 | Michelson | |
| 7,972,363 B2 | 7/2011 | Moskowitz et al. | |
| 7,976,566 B2 | 7/2011 | Michelson | |
| 8,002,837 B2 | 8/2011 | Stream et al. | |
| 8,070,816 B2 | 12/2011 | Taylor | |
| 8,100,975 B2 | 1/2012 | Waugh et al. | |
| 8,100,976 B2 | 1/2012 | Bray et al. | |
| 8,268,000 B2 | 9/2012 | Waugh et al. | |
| 8,343,219 B2 | 1/2013 | Allain et al. | |
| 8,343,223 B2 | 1/2013 | Bucci | |
| 8,377,132 B2 | 2/2013 | Wing et al. | |
| 8,382,843 B2 | 2/2013 | Laurence et al. | |
| 8,414,651 B2 | 4/2013 | Tyber et al. | |
| 8,425,514 B2 | 4/2013 | Anderson et al. | |
| 8,480,747 B2 | 7/2013 | Melkent et al. | |
| 8,486,149 B2 | 7/2013 | Saidha et al. | |
| 8,523,947 B2 | 9/2013 | Theofilos | |
| 8,540,774 B2 | 9/2013 | Kueenzi et al. | |
| 8,613,772 B2 | 12/2013 | Bray et al. | |
| 8,641,765 B2 | 2/2014 | Muhanna | |
| 8,685,104 B2 | 4/2014 | Lee et al. | |
| 8,734,516 B2 | 5/2014 | Moskowitz et al. | |
| 9,005,295 B2 | 4/2015 | Kueenzi et al. | |
| 9,155,631 B2 | 10/2015 | Seifert et al. | |
| 9,220,609 B2 | 12/2015 | Mueller et al. | |
| 9,375,237 B2 | 6/2016 | Keegan et al. | |
| 2005/0085913 A1 | 4/2005 | Fraser et al. | |
| 2006/0129244 A1 | 6/2006 | Ensign | |
| 2007/0106384 A1 | 5/2007 | Bray et al. | |
| 2007/0225707 A1 | 9/2007 | Wisnewski et al. | |
| 2008/0133014 A1 | 6/2008 | Gately et al. | |
| 2008/0161925 A1 * | 7/2008 | Brittan | A61F 2/4465 623/17.16 |
| 2008/0177307 A1 * | 7/2008 | Moskowitz | A61B 17/0642 606/246 |
| 2008/0249569 A1 | 10/2008 | Waugh et al. | |
| 2008/0281425 A1 | 11/2008 | Thalgott et al. | |
| 2008/0300634 A1 * | 12/2008 | Gray | A61B 17/7059 606/280 |
| 2008/0300685 A1 | 12/2008 | Carls et al. | |
| 2009/0088849 A1 | 4/2009 | Armstrong et al. | |
| 2009/0182430 A1 * | 7/2009 | Tyber | A61F 2/4465 623/17.16 |
| 2009/0210062 A1 | 8/2009 | Thalgott et al. | |
| 2009/0248076 A1 | 10/2009 | Reynolds et al. | |
| 2009/0306779 A1 | 12/2009 | Ahn | |
| 2009/0326580 A1 * | 12/2009 | Anderson | A61B 17/7059 606/246 |
| 2010/0004747 A1 | 1/2010 | Lin | |
| 2010/0057206 A1 | 3/2010 | Duffield et al. | |
| 2010/0145459 A1 * | 6/2010 | McDonough | A61B 17/8033 623/17.16 |
| 2010/0305704 A1 | 12/2010 | Messerli et al. | |
| 2010/0312346 A1 | 12/2010 | Kueenzi et al. | |
| 2011/0015745 A1 | 1/2011 | Bucci | |
| 2011/0166657 A1 | 7/2011 | Thalgott et al. | |
| 2011/0166658 A1 | 7/2011 | Garber et al. | |
| 2011/0184415 A1 | 7/2011 | Anderson et al. | |
| 2011/0190889 A1 | 8/2011 | Miller et al. | |
| 2011/0224793 A1 | 9/2011 | Fortin et al. | |
| 2011/0230971 A1 | 9/2011 | Thomas | |
| 2011/0251689 A1 | 10/2011 | Seifert et al. | |
| 2012/0029639 A1 | 2/2012 | Blackwell et al. | |
| 2012/0041559 A1 | 2/2012 | Melkent et al. | |
| 2012/0078373 A1 | 3/2012 | Gamache et al. | |
| 2012/0136392 A1 | 5/2012 | Keegan et al. | |
| 2012/0172989 A1 | 7/2012 | McCarthy | |
| 2012/0277867 A1 | 11/2012 | Kana et al. | |
| 2013/0073045 A1 | 3/2013 | Vestgaarden | |
| 2013/0166027 A1 | 6/2013 | Bellas | |
| 2013/0166029 A1 | 6/2013 | Dinville et al. | |
| 2013/0226300 A1 | 8/2013 | Chataigner et al. | |
| 2013/0238095 A1 | 9/2013 | Pavento et al. | |
| 2013/0282126 A1 | 10/2013 | Saidha et al. | |
| 2013/0297029 A1 | 11/2013 | Kana et al. | |
| 2013/0345813 A1 | 12/2013 | Frank et al. | |
| 2014/0039623 A1 | 2/2014 | Iott et al. | |
| 2014/0046447 A1 | 2/2014 | Dunworth et al. | |
| 2014/0114423 A1 | 4/2014 | Suedkamp et al. | |
| 2014/0148905 A1 | 5/2014 | Messerli et al. | |
| 2014/0163682 A1 | 6/2014 | Iott et al. | |
| 2014/0277497 A1 | 9/2014 | Bennett et al. | |
| 2016/0262905 A1 * | 9/2016 | Prado | A61F 2/447 |
| 2018/0303521 A1 * | 10/2018 | Hynes | A61B 17/7059 |

FOREIGN PATENT DOCUMENTS

| | | |
|---|---|---|
| CA | 2551185 | 3/1995 |
| CN | 1575780 | 2/2005 |
| CN | 101415374 | 4/2009 |
| CN | 101878007 | 11/2010 |
| CN | 101909551 | 12/2010 |
| CN | 102438556 | 5/2012 |
| EP | 1617772 | 1/2006 |
| EP | 1834608 | 9/2007 |
| EP | 2628467 | 8/2013 |
| GB | 2457673 | 8/2009 |
| JP | 2006-524114 | 10/2006 |
| JP | 2011-502708 | 1/2011 |
| JP | 2011-062539 | 3/2011 |
| WO | 2004/093654 | 11/2004 |

(56) References Cited

FOREIGN PATENT DOCUMENTS

| WO | 2006/019370 | 2/2006 |
|----|-------------|--------|
| WO | 2007/098288 | 8/2007 |
| WO | 2009/064644 | 5/2009 |
| WO | 2010/107692 | 9/2010 |

OTHER PUBLICATIONS

Examination Report, dated Jun. 1, 2017, received in connection with corresponding EP Patent Application No. 13739320.3.
Search Report, dated Nov. 19, 2015, received in connection with corresponding CN Patent Application No. 201380034687.4 (English Translation).
International Preliminary Report on Patentability and Written Opinion, dated Dec. 31, 2014, received in connection with corresponding International Application No. PCT/US2013/048973.
International Search Report and Written Opinion, dated Nov. 4, 2013, received in connection with corresponding International Patent Application No. PCT/US2013/048973.

\* cited by examiner

LATERAL INSERTION SPINAL IMPLANT

CROSS-REFERENCE TO RELATED APPLICATIONS

This application is a continuation of U.S. application Ser. No. 13/932,771, filed Jul. 1, 2013 (now U.S. Pat. No. 9,943,417), which claims priority to U.S. Provisional Patent Application No. 61/666,335, filed Jun. 29, 2012, each entitled "Lateral Insertion Spinal Implant," which are incorporated herein by reference in their entirety.

BACKGROUND

Spondylolisthesis is a term used to describe when one vertebrae slips forward on the vertebrae below it. This usually occurs because there is a spondylolysis in the superior vertebrae. There are two main parts of the spine that keep the vertebrae aligned, which include the disc and the facet joints. When spondylolysis occurs, the facet joint can no longer hold the vertebrae back. The intervertebral disc may slowly stretch under the increased stress and allow the upper vertebra to slide forward. In the vast majority of cases, stretching of the intervertebral disc only allows for a small amount of forward slip.

Surgical treatment for spondylolisthesis needs to address both the mechanical symptoms and the compressive symptoms, if they are present. The goals of surgery are to remove pressure on spinal nerves (i.e., decompression) and to provide stability to the thoracic/lumbar spine. In most cases of spondylolisthesis, decompression should be accompanied by uniting one spinal vertebrae to the next (i.e., spinal fusion) with spinal instrumentation (i.e., implants that are often used to help aid the healing process).

In other cases, the spinal disc and/or vertebral bodies may be displaced or damaged due to trauma, disease, degenerative effects, or wear over an extended period of time. This displacement or damage often causes chronic back pain. In order to alleviate the chronic back pain, a spinal disc is removed, along with all or part of at least one of the neighboring vertebrae. An implant is then inserted to promote fusion of the remaining bony anatomy. The success of spinal fusion is limited, however, due to several factors. For example, the spacer or implant or cage used to fill the space left by the removed disc may not be strong enough to support the spine. Furthermore, the spacer must be able to remain in the position in which it is placed by the surgeon. The space must also be comprised of such a material to promote bony growth around the spacer and within the spinal region.

SUMMARY

The present disclosure relates to spinal implants. For example, the spinal implants may be used for insertion into the intervertebral disc space. The spinal implants may also be used for alleviating chronic back pain and promoting bony growth around the spinal implants. The spinal implants may also be positioned between two vertebral bodies and secured with at least two locking screws.

An example spinal implant includes an intervertebral spacer body, a plate, and at least two screws. The intervertebral spacer body includes a pair of opposite sides. The plate comprises a front surface and a rear surface. The plate is configured to attach to vertebral bodies by at least two screws. For example, the plate includes at least one upper borehole and at least one lower borehole for attachment of the plate to the vertebral bodies. The plate may comprise at least two lower boreholes and the at least two upper boreholes, which are off-centered about the centerline of the plate.

The plate is configured to mate with the intervertebral spacer body. A portion of the rear surface of the plate is adapted to contact a wall of a vertebral body. Each borehole comprises a threaded region adapted to engage a complementary threaded region of a head of a screw inserted therethrough at a fixed angle relative to the plate. Further, the screws inserted into the at least two upper boreholes and the at least two lower boreholes have divergent angles. The screws diverge asymmetrically about a transverse midline of the plate.

The pair of opposite sides of the intervertebral spacer body may also contact two vertebral bodies. The anterior portion of the intervertebral spacer body optionally curves medially. The screws may include at least two anterior screws and at least two posterior screws.

The spinal implant may also include screws that are locking screws. The plate optionally has conical locking threads in the boreholes. The locking screws may be screwed into the plate and locked into the conical locking threads in the boreholes. The screws, locking or non-locking, may also be inserted into the first and second vertebral bodies at divergent angles, or where the screws diverge either symmetrically or asymmetrically about the transverse midline.

The intervertebral spacer body may also include a plurality of protrusions. These protrusions optionally secure the intervertebral spacer body between the first and second vertebral bodies. The plate of the spinal implant may also include at least three boreholes, and in other embodiments, it may contain at least two boreholes.

These and other features and advantages of the implementations of the present disclosure will become more readily apparent to those skilled in the art upon consideration of the following detailed description and accompanying drawings, which describe both the preferred and alternative implementations of the present disclosure.

BRIEF DESCRIPTION OF THE DRAWINGS

In the drawings, like reference numbers and designations in the various drawings indicate like elements.

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a," "an," and "the," include plural referents unless the context clearly dictates otherwise. The term "comprising" and variations thereof as used herein is used synonymously with the term "including" and variations thereof and are open, non-limiting terms.

In performing a wide range of back surgeries, surgeons are often required to make use of pedicle screws and rods. These pedicle screws and rods are components of rigid stabilization systems, which tend to be intrusive to surrounding tissue and vasculature systems. The present disclosure is less intrusive because this spinal implant not only is conformable to the spinal anatomy, but also is strong enough to allow surgeons to avoid using pedicle screws and rods. The present disclosure also allows for less invasive surgery and quicker surgery time.

Figure 1:
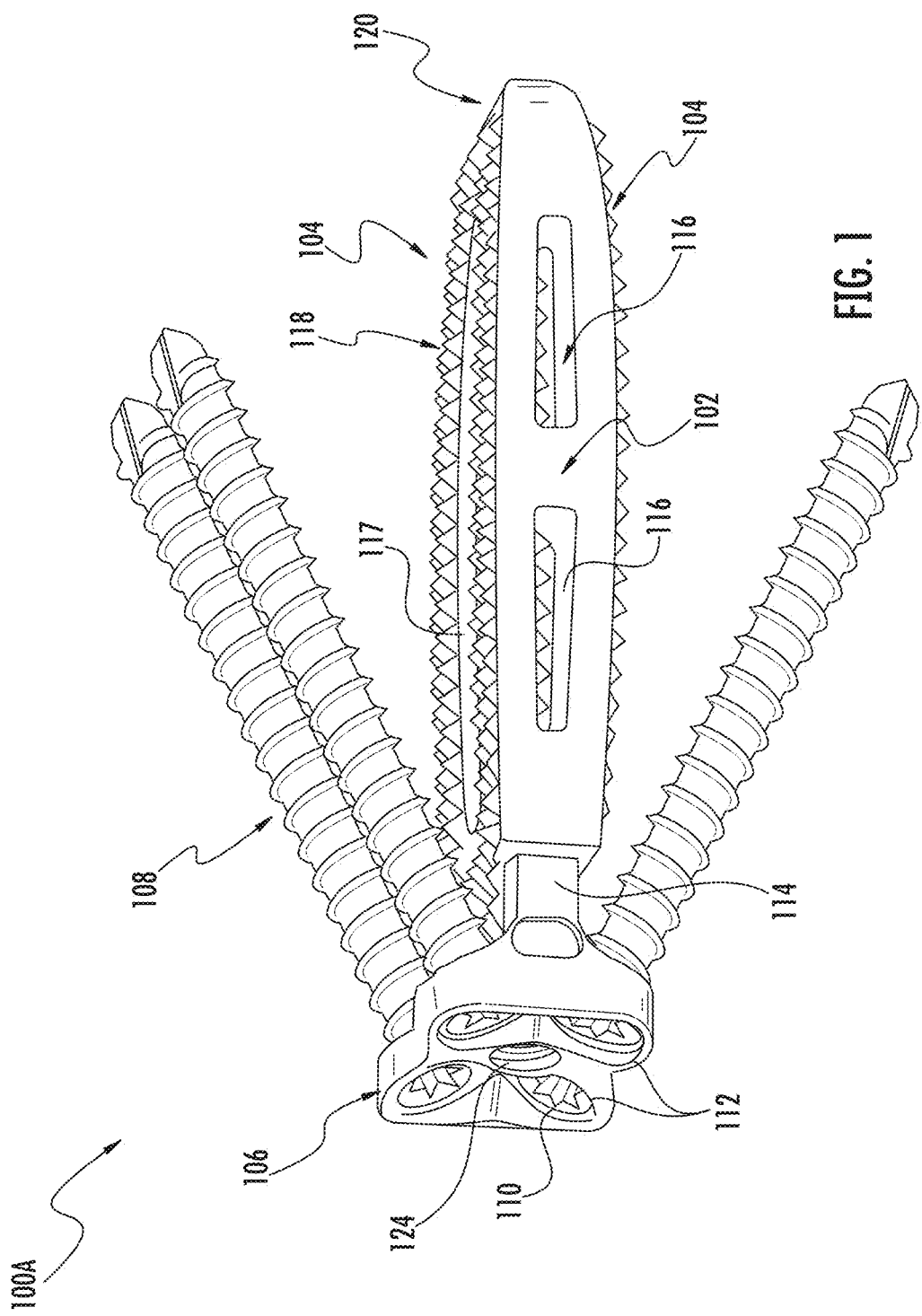
FIG. 1 is a perspective view of an example spinal implant.

FIGS. 1-18 illustrate the different views of an embodiment of the present disclosure. An example spinal implant 100A is shown in FIG. 1. FIG. 1 serves as an introduction to the components and features of the spinal implant 100A. Details of the various components of the spinal implant 100A are illustrated in FIGS. 2-11. The spinal implant 100A includes an intervertebral spacer body 102 and a plate 106. The intervertebral spacer body 102 includes a pair of opposite sides 104. Each opposite side 104 optionally has pyramid-shaped teeth 118 that are provided to frictionally engage top and bottom surfaces of a vertebral body. The intervertebral spacer body 102 may include a central window 117 and side windows 116. Tantalum markers may be provided proximate to the central and side windows 116. A surgeon or any other medical professional may take radiographs of the area in which a spinal implant 100A is placed to view the tantalum markers to insure proper placement of the implant 100A in a patient's body. The intervertebral spacer body 102 may include a self-distracting bulletnose 120. The intervertebral spacer body 102 is optionally made of polyether ether ketone (PEEK), any other biocompatible materials appropriate for medical implants.

The plate 106 is comprised of a front surface and a rear surface. The plate 106 may include at least two upper boreholes 110 and at least two lower boreholes 110, respectively positioned about a centerline and through the front surface and the rear surface of the plate 106. The at least two upper boreholes 110 and the at least two lower boreholes 110 may have one or more alignments within the plate 106 and with respect to the centerline of the plate 106. A further discussion of the boreholes 110 is provided below with reference to FIGS. 6-9. The plate 106 further includes coupling flanges 114 that are adapted to be coupled to the spacer body 102. The plate 106 may also define a region to mate with the intervertebral spacer body 102. For example, a portion of the rear surface of the plate 106 is adapted to contact a wall of the vertebral body. A central hole 124 is provided as an insertion region into which a screw (not shown) may be inserted to secure the plate 102 to the spacer body 102 and/or attachment of an appropriate insertion device. The plate 106 may comprise TAN, any other titanium alloy appropriate for surgical or medical devices, or any other appropriate material.

One or more screws 108 attach the plate 106 to the vertebral bodies and to secure the intervertebral spacer body 102 therein between. The screws 108 optionally comprise a titanium-6 aluminum-7 niobium alloy (TAN), any other titanium alloy appropriate for surgical or medical devices, or any other appropriate material.

As will be described with reference to FIGS. 2-7, the first embodiment of the spinal implant 100A include many different combinations of spacer bodies 102A-102D and plates 106A-106D. In particular, the various spacer bodies 102A-102D are illustrated in FIGS. 2-5, which may be interchangeably attached with the plates 106A-106D illustrated in FIGS. 6-9 to create a spinal implant 100A having a configuration adapted for use in a specific regions of the spinal column.

Figure 2A:
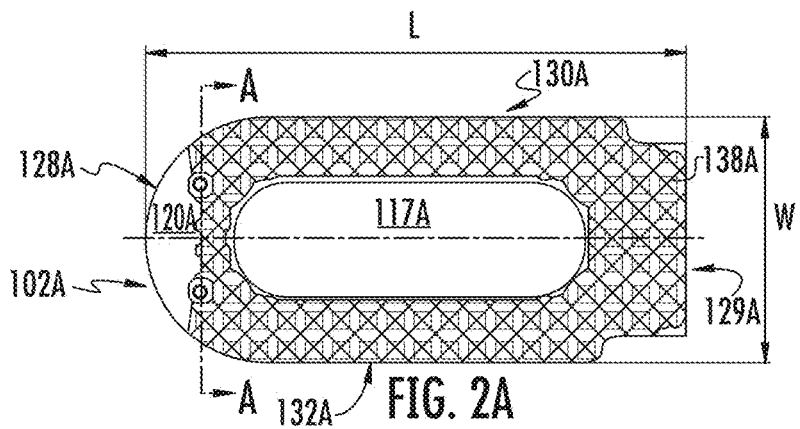
FIGS. 2A-2F illustrate a first embodiment of a spacer body that may be used to construct the spinal implant of FIG. 1.
Figure 2B:
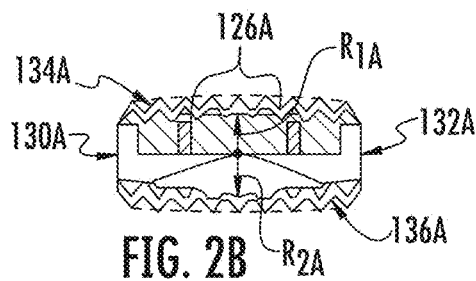
Figure 2C:
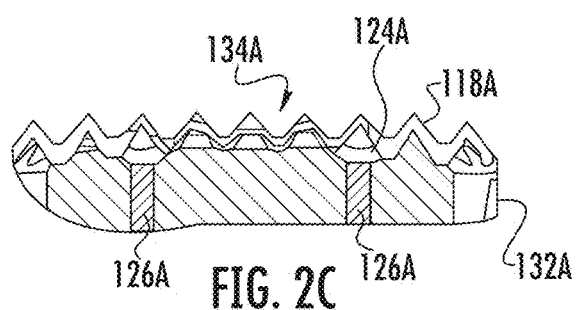
Figure 2D:
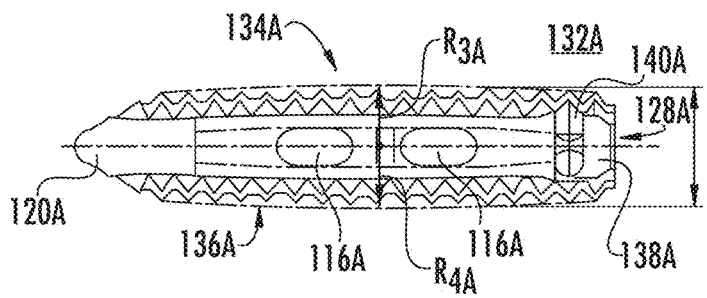

FIGS. 2A-2F illustrate a first embodiment of a spacer body 102A that may be used to construct the spinal implant 100A of the present disclosure. As illustrated in FIGS. 2A and 2D, the spacer body 102A includes a generally rounded distal end 128A and a proximal end 129A that defines a base 138A that is adapted to engage the coupling flanges 114 of the plate 106. The spacer body 102A has either straight or non-straight sides 130A and 132A and a central window 117A. The central window 117A is generally an oval shape, but can be any shape or shapes, such as one or more circular regions, rectangular regions, polygon-shaped regions, etc. The central window 117A may promote the growth of a bony bridge between adjacent vertebral bodies within which the spacer body 102A is inserted. In accordance with the first embodiment, the spacer body 102A may have a width W of approximately 18 mm and a length L of approximately 35 to 55 mm. Thus, the spacer body 102A may have a length to width ratio of approximately 1.8-3.2 when used for, e.g., lateral procedures.

As shown in the cross sectional view of FIG. 2B and the magnified view of FIG. 2C, the top surface 134A and the bottom surface 136A have a radius of curvature denoted $R_{1A}$ and $R_{2A}$, respectively between the sides 130A and 132A. Thus, the top surface 134A and the bottom surface 136A are slightly curved in a lateral direction of the spacer body 102A. The radius of curvature $R_{1A}$ and $R_{2A}$ may be the same or different to achieve a secure fit with an adjacent vertebral body. FIGS. 2B and 2C illustrate pins 126A, which may be viewed using an appropriate imaging device to confirm the location of the spinal implant 100A when inserted into a patient's body. The pins 126A may have a width of approximately 0.8 mm and may be made from, e.g., stainless steel or other material that is visible when exposed to, e.g., x-rays.

Figure 2E:
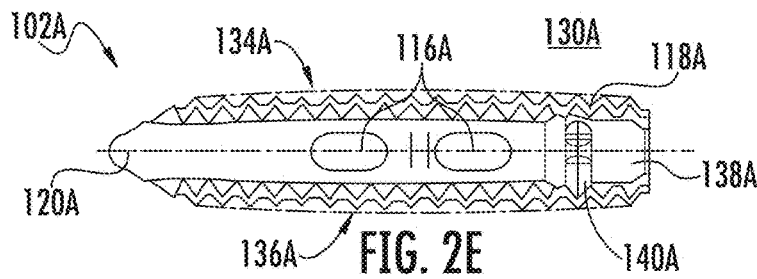

As shown in FIGS. 2D and 2E, the top surface 134A and the bottom surface 136A of spacer body 102A also have a radius of curvature $R_{3A}$ and $R_{4A}$, respectively, between the distal and 128A and the proximal end 129A. As such, the top surface 134A and the bottom surface 136A are slightly curved in the longitudinal direction of the spacer body 102A. The radius of curvature $R_{3A}$ and $R_{4A}$ may be the same or different to achieve a secure fit with an adjacent vertebral body. The curvature of the top surface 134A and bottom surface 136A in the lateral and/or longitudinal directions provides a shape that may be received within natural contours of the vertebral bodies.

FIGS. 2D and 2E also illustrate the side windows 116A and the pyramid-shaped teeth 118A in greater detail. The side widows 116A may have any suitable geometry, including but not limited to, oval, oblong, rectangular, triangular, circular, polygonal and/or any combination thereof. The teeth 118A may have other shapes suitable for engaging the vertebral bodies. Recesses 140A are defined in the sides 130A and 132A receive inward pointing projections 150A/150B and 152A/152B (see, FIGS. 6-7) of the coupling flanges 114 in order to snap the plate 106 securely into place on the spacer body 102A. In some implementations, the recess 140A extend along only a portion of the side walls 130A and 132A. In accordance with the present disclosure, the spacer body 102A may have a height H of approximately 6 mm to 17 mm.

Figure 2F:
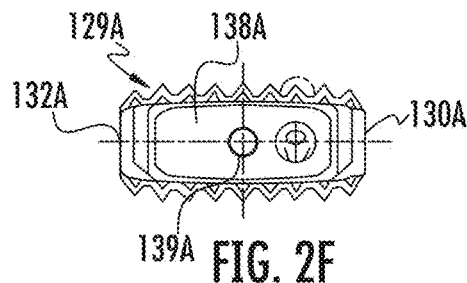

FIG. 2F illustrates view of the proximal end 129A of the spacer body 102A. The base 138A is defined having a width that is narrower than the overall width of the spacer 102A (see, FIG. 2A), such that when the coupling flanges 114 are joined thereto, the overall width of the base 138A and the coupling flanges 114 is approximately equal to the width of the spacer body 102A. For example, the width of the base 138A may be sized such that may be securely grasped between the coupling flanges 114 of the plate 106. The base 138A may further define a hole 139A which may receive a screw (not shown) used to secure the plate 106 to the spacer body 102A, either solely for insertion or for long term connection.

Thus, as shown in FIGS. 2A-2F and described above, a medical specialist can select an appropriately sized spacer body 102A in accordance with the void between adjacent vertebral bodies into which the spacer body will be inserted.

FIGS. 3A-3F illustrate a second embodiment of a spacer body 102B that may be used to construct the spinal implant 100A of the present disclosure. Aspects of the spacer body 102B that are substantially similar to the first embodiment of the spacer body 102A will not be repeated.

Figure 3A:
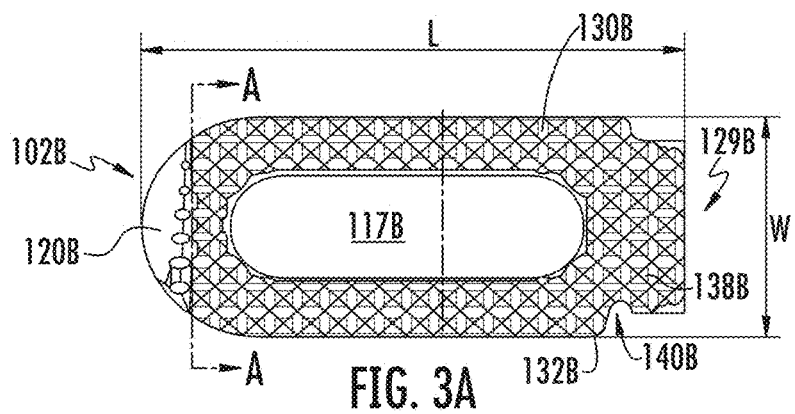
FIGS. 3A-3F illustrate a second embodiment of a spacer body that may be used to construct the spinal implant of FIG. 1.
Figure 3B:
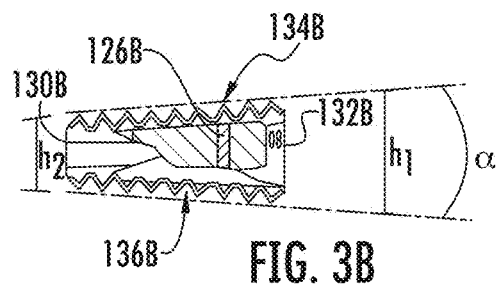
Figure 3C:
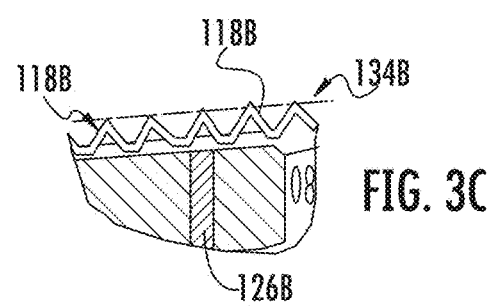

As shown in the cross sectional view of FIG. 3B and the magnified view of FIG. 3C, the top surface 134B and the bottom surface 136B each are substantially flat. As shown, the side 132B has a height of $h_1$ and the side 130B has a height of $h_2$. Thus, the top surface 134A and the bottom surface 136A form an angle α that is defined by the heights $h_1$ and $h_2$. In accordance with the present disclosure the heights $h_1$ and $h_2$ may range from approximately 5 mm to 17 mm.

Figure 3D:
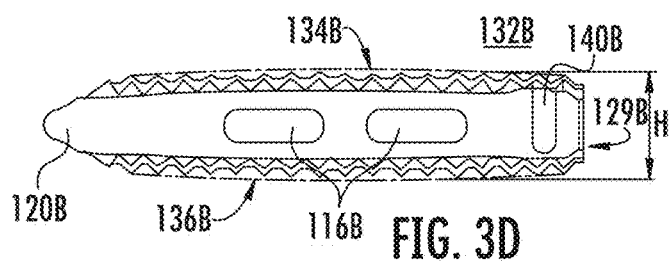
Figure 3E:
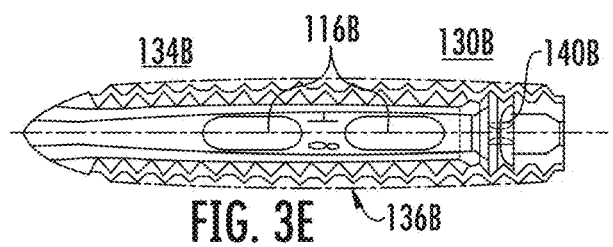

As shown in FIG. 3E, a recess 140B defined in the side 130B extends along the entirety of the side wall 130B, where a recess 140B formed in the side 132B extends along a portion of the side 132B (see, FIGS. 3A and 3D).

Figure 3F:
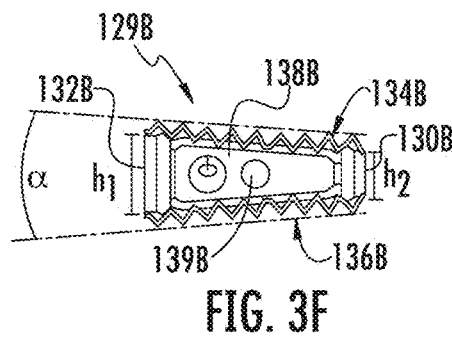

FIG. 3F illustrates view of the proximal end 129B of the spacer body 102B. The base 138B is defined having a width that is narrower than the overall width of the spacer 102B (see, FIG. 3A), such that when the coupling flanges 114 are joined thereto, the overall width of the base 138B and the coupling flanges 114 is approximately equal to the width of the spacer body 102B. The base 138B may further define a hole 139B which may receive a screw (not shown) used to secure the plate 106 to the spacer body 102B. As illustrated, the base 138B is formed having at the same angle α that is defined by the heights $h_1$ and $h_2$ of the sides 132B and 130B, respectively.

Thus, as shown in FIGS. 3A-3F and described above, a medical specialist can select an appropriately sized spacer body 102B in accordance with the void between adjacent vertebral bodies into which the spacer body will be inserted.

Figure 4A:
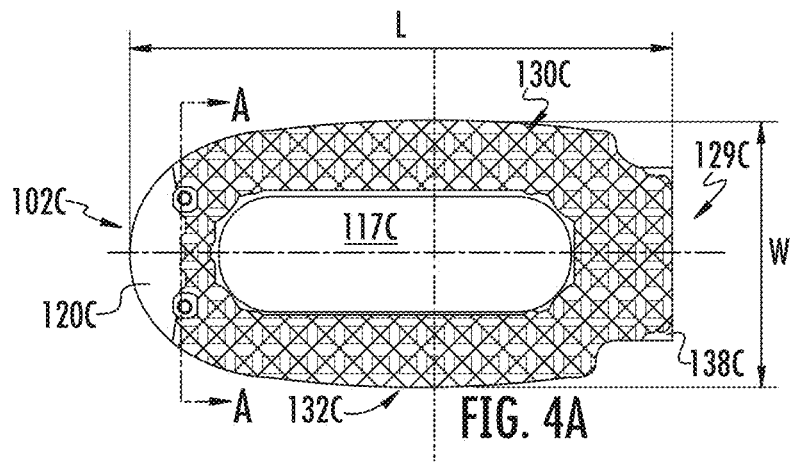
FIGS. 4A-4F illustrate a third embodiment of a spacer body that may be used to construct the spinal implant of FIG. 1.
Figure 4B:
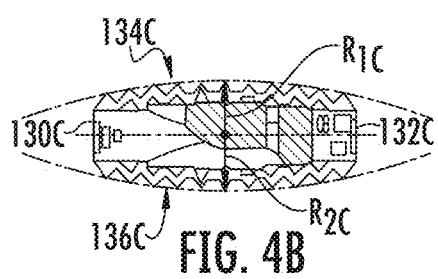
Figure 4C:
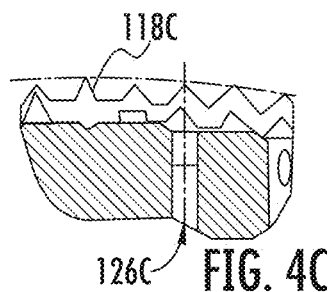
Figure 4D:
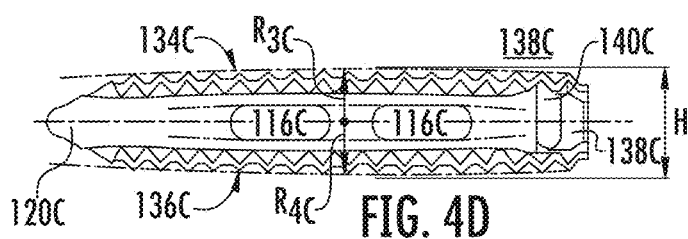
Figure 4E:
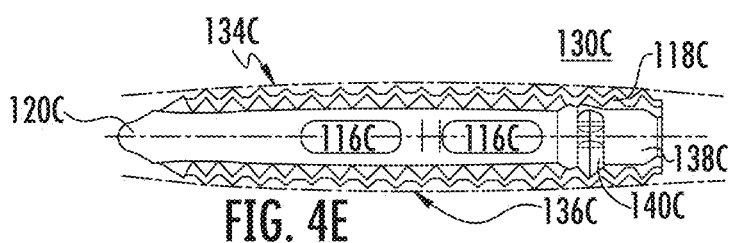
Figure 4F:
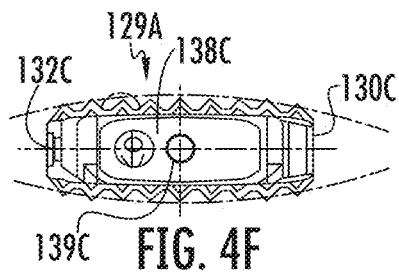

FIGS. 4A-4F illustrate a third embodiment of a spacer body 102C that may be used to construct the spinal implant 100A of the present disclosure. Those aspects of the third embodiment of the spacer body 102C that are substantially similar to the first embodiment of the spacer body 102A will not be repeated below. As illustrated in FIGS. 4A and 4D, the spacer body 102C includes a generally rounded distal end 128C and a proximal end 129C that defines a base 138C that is adapted to engage the coupling flanges 114 of the plate 106. The spacer body 102C has curved sides 130C and 132C and a central window 117C. In accordance with the third embodiment, the spacer body 102C may have a width W of approximately 22 mm (as measured between the widest points) and a length L of approximately 35 to 55 mm. Thus, the spacer body 102C may have a length to width ratio of approximately 1.59-2.5 when used for, e.g., lateral procedures.

Thus, as shown in FIGS. 4A-4F and described above, a medical specialist can select an appropriately sized spacer body 102C in accordance with the void between adjacent vertebral bodies into which the spacer body will be inserted.

FIGS. 5A-5F illustrate a fourth embodiment of a spacer body 102D that may be used to construct the spinal implant 100A of the present disclosure. Aspects of the spacer body 102D that are substantially similar to the second embodiment of the spacer body 102B will not be repeated.

Figure 5A:
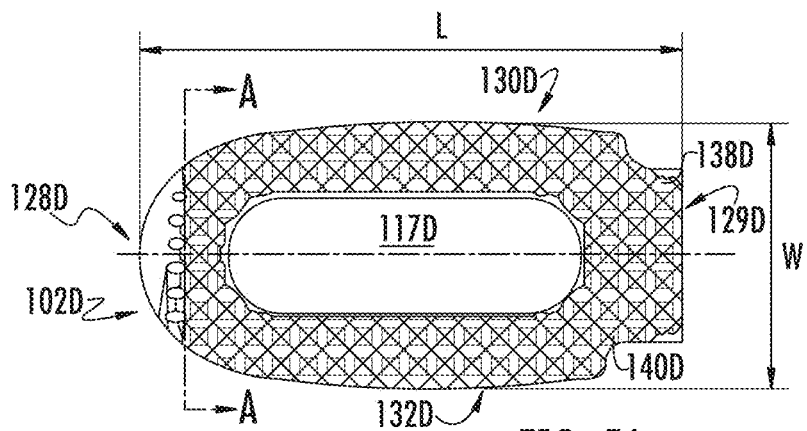
FIGS. 5A-5F illustrate a fourth embodiment of a spacer body that may be used to construct the spinal implant of FIG. 1.
Figure 5B:
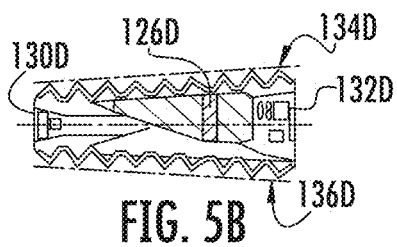
Figure 5C:
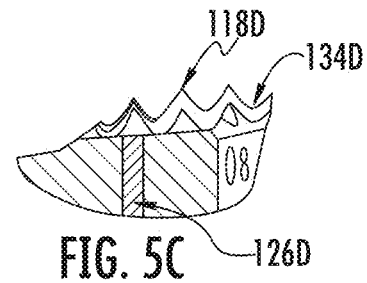
Figure 5D:
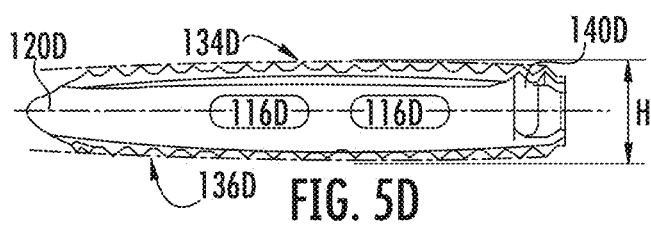
Figure 5E:
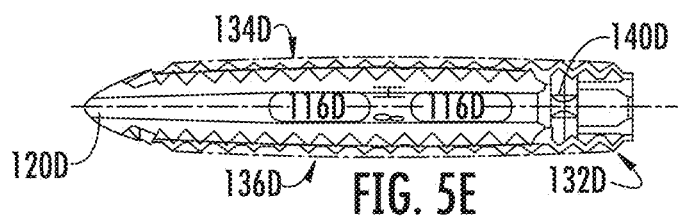
Figure 5F:
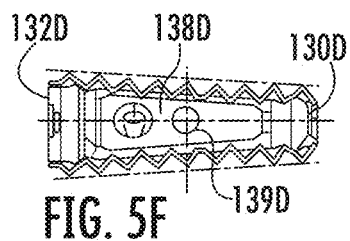

As illustrated in FIGS. 5A and 5D, the spacer body 102C includes curved sides 130C and 132C and a central window 117C. In accordance with the fourth embodiment, the spacer body 102D may have a width W of approximately 22 mm (as measured between the widest points) and a length L of approximately 35 to 55 mm. Thus, the spacer body 102D may have a length to width ratio of approximately 1.59-2.5 when used for, e.g., lateral procedures.

Thus, as shown in FIGS. 5A-5F and described above, a medical specialist can select an appropriately sized spacer body 102D in accordance with the void between adjacent vertebral bodies into which the spacer body will be inserted.

Figure 6E:
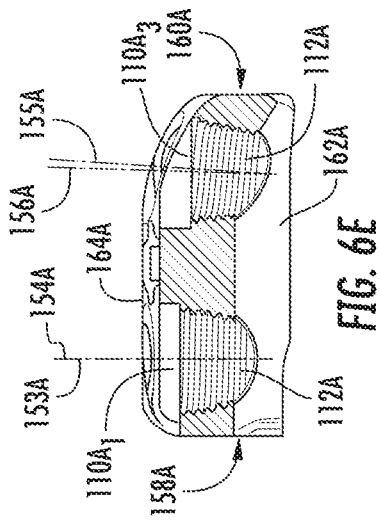
FIGS. 6A-6H illustrate a plate in accordance with a first embodiment of the present disclosure.
Figure 6F:
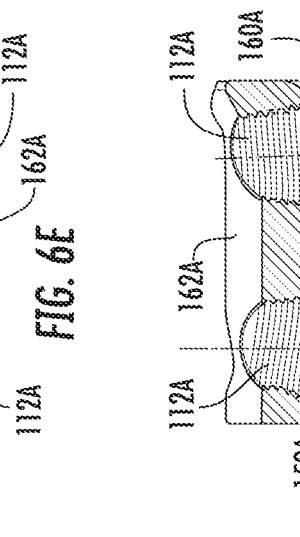
Figure 6B:
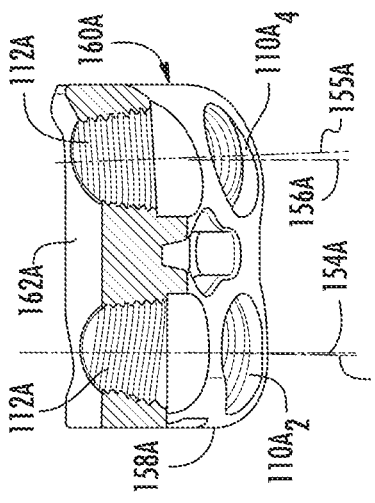
Figure 6D:
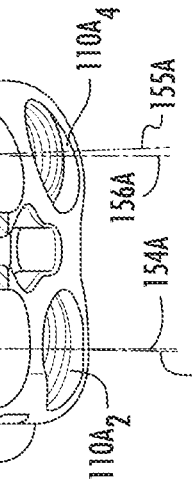
Figure 6H:
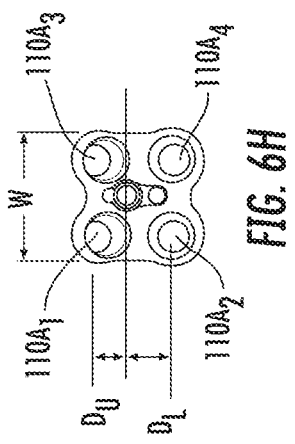
Figure 6A:
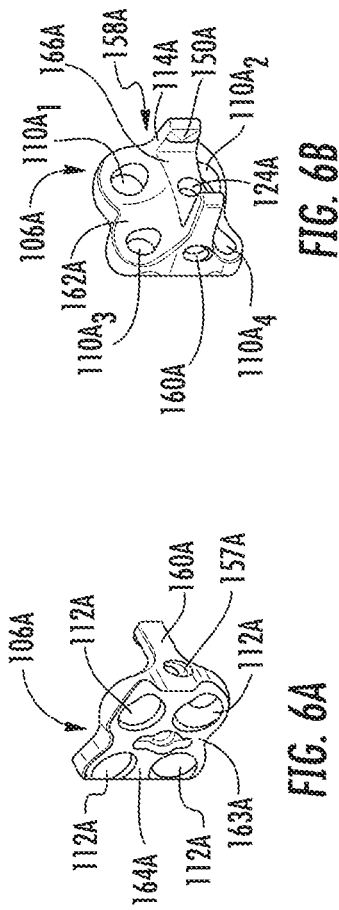

FIGS. 6A-6H illustrate a plate 106A in accordance with a first embodiment of the present disclosure. The first embodiment illustrates a so-called "asymmetric plate" in accordance with the present disclosure. FIGS. 6A and 6B, respectively, illustrate front and rear perspective views of the plate 106A. The plate 106A includes sides 158A and 160A, a rear surface 162A and a front surface 164A. Circular recesses 157A may be formed in the sides 158A and 160A of the plate 106A. A central hole 124A is provided into which a screw (not shown) may be inserted to secure the plate 106A to the various spacer bodies described above. The central hole 124A may be formed within a keyed recess 163A.

In FIG. 6B, there is shown the coupling flanges 114A and their associated inward pointing projections 150A and 152A. As noted above, the projections 150A and 152A are received within the recesses 140 of the base 138 of the spacer bodies 102, as described above. The coupling flanges 114A extend from a substantially flat wall 166A that abuts the base 138 of the spacer body 102 when the plate 106A is attached thereto. As shown in FIGS. 6A and 6B, the boreholes $110_{A1}$ to $110_{A4}$ may include locking threads 112A that are adapted to receive complementary threads of the screws 108.

Figure 6C:
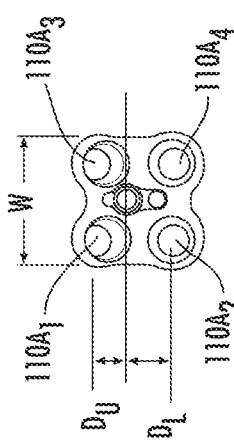

Referring now to FIG. 6C, there is shown a side view of the plate 106A showing the side 160A. The lower boreholes $110_{A2}$ and $110_{A4}$ may be have a central axis 153A that is formed at an approximately 5° angle with respect to a first horizontal axis 154A passing through the center of the boreholes $110_{A2}$ and $110_{A4}$ that parallels a lateral center plane 161A of the plate 106A. As shown in the side view of FIG. 6D illustrating the side 158A, the upper boreholes $110_{A1}$ and $110_{A3}$ may have a central axis 155A that is formed at an approximately 20° angle with respect to a second horizontal axis 156A passing through the center of the boreholes $110_{A1}$ and $110_{A3}$ that parallels the lateral center plane 161A.

As will be shown in FIGS. 15A-16B the above offsets of the central axis causes the screws 108 inserted therein to diverge at asymmetric angles about the lateral center plane 161A of the plate 106A. It is noted that central axis 153A and 155A of the lower and upper boreholes may be offset at any angle between 5° and 20° with respect to the horizontal axis 154A and 156A. It is also noted that central axis of the upper boreholes and lower boreholes may be at the same angle with respect to the horizontal axis 154A and 156A, thus causing the screws inserted therein to diverge at symmetrically angles about the lateral center plane 161A of the plate 106A.

FIG. 6F illustrates a cross-sectional view of the lower boreholes $110_{A2}$ and $110_{A4}$ shown in FIG. 6C. FIG. 6F illustrates a cross-sectional view of the upper boreholes $110_{A1}$ and $110_{A3}$ shown in FIG. 6D. As illustrated in FIGS. 6E and 6F, locking threads 112A are defined within the boreholes $110_{A1}$-$110_{A4}$ to threadedly engage with complementary locking threads of the head of the screw 108. In accordance with the first embodiment, the upper and lower boreholes $110_{A3}$ and $110_{A4}$ may have a central axis 155A and 153A that are laterally offset at approximately a 3° angle with respect to the second horizontal axis 156A and first horizontal axis 154A, respectively, passing through the center of the boreholes $110_{A3}$ and $110_{A4}$. The upper and lower boreholes $110_{A1}$ and $110_{A2}$ formed proximate to the side 158A may have a central axis 155A and 153A that are laterally offset at approximately a 1° angle with respect to the second horizontal axis 156A and first horizontal axis 154A, respectively, passing through the center of the boreholes $110_{A1}$ and $110_{A2}$. The first horizontal axis 154A and the second horizontal axis 156A parallel a longitudinal central plane 165A (see, also FIG. 6H) of the plate 106A.

Each of the boreholes $110_{A1}$-$110_{A4}$ may be tapered such that it is wider proximate to the front surface 164A than proximate to the rear surface 162A forming a conical surface therein. As such, a screw inserted having a complementary taper will stop at a predetermined position within the plate 106A. As shown, the centers of boreholes $110_{A1}$ and $110_{A2}$ may be positioned 5.3 mm from a center of the plate 106A, whereas the boreholes $110_{A3}$ and $110_{A4}$ may be positioned 5.5 mm from the center of the plate 106A, as defined by the longitudinal central plane 165A.

Figure 6G:
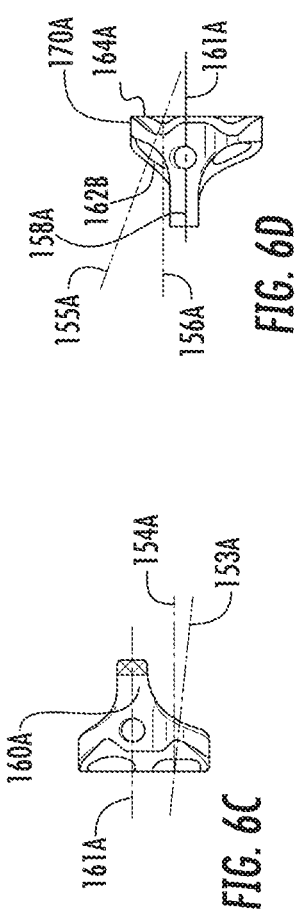

Referring now to FIG. 6G, there is illustrated a top view of the plate 106A. The rear surface 162A forms a curved surface moving longitudinally from a top 170A of the plate 106A to the flat wall 166A (see, also FIG. 6B). Although not shown in FIG. 6G, the rear surface 162A forms a similar curved surface moving longitudinally from a bottom 172A of the plate 106A to the flat wall 166A. As illustrated, the top surface 170A is generally medially curved from the side 158A to the side 160A, forming a region 174A that substantially matches a curvature an outer wall of a superior vertebral body. A similar curved region is formed from the side 158A to the side 160A proximate to the bottom 172A that substantially matches a curvature an outer wall of an inferior vertebral body. In particular, the curved region 174A (and lower curved region (not shown)) may have a portion thereof having a radius of curvature $R_{6A}$ formed proximate to the edge of the front surface 164A and the side 160A. In addition, the edge formed by the front surface 164A and the side 158A may be formed having a radius of curvature $R_{5A}$.

As shown in FIG. 6G, in some implementations, the coupling flanges 114A may be of unequal length. The coupling flanges 114A may each have the inward pointing projections 150A and 152B, respectively, as described above, for engaging the recesses 140 of the spacer body 102. For example, a flange extending alongside 158A may have a length of 15 mm, as measured from the front surface 164A. A flange extending alongside 160A may have a length of 13 mm, as measured from the front surface 164A. The flanges may be formed having equal lengths, or any combination of lengths between 12 mm and 16 mm. The inner walls of the flanges may be separated by distance $H_F$ of 14 mm. The distance $H_F$ may be any value that is substantially equal to a width of the base 138 of the spacer bodies described above. The width W of the plate 106A is approximately 19 mm.

FIG. 6H illustrates a front view of the plate 106A. As illustrated, the upper boreholes $110_{A1}$ and $110_{A3}$ may be located a distance $D_U$ from the lateral center plane 161A and about the longitudinal center plane 165A. Lower boreholes $110_{A2}$ and $110_{A4}$ may be located a distance $D_L$ from a lateral center plane 161A and about the longitudinal center plane 165A. The distance $D_U$ may range from approximate 2.75 mm to 6.75 mm. The distance $D_L$ may range from approximately 6 mm to 10 mm. Thus, the ratio of $D_L:D_U$ is approximately 1.4 to 2.2. The plate 106A may have a height H that ranges from approximately 18 mm to 26 mm. The distance Q between the outer edges of the boreholes in a vertical direction may range from approximately 15 mm to 23 mm, thus providing approximately 1.5 mm of material between the outer edge of the borehole and the edge of the plate 106A. The distance U between the inner edges of the boreholes may range from approximately 2.5 mm to 10.5 mm. Also as shown in FIG. 6H, the front surface 164A defines a substantially rectangular region having dimples 176A and 178A formed along the outer edges of the plate 106A between the boreholes. The plate 106A may have a width of approximately 18 mm, as measured between the dimples formed in the sides 158A and 160A. Thus, the dimples 176A and 178A remove approximately 1 mm of material, reducing the weight of the plate 106A.

Thus, as shown in FIGS. 6A-6H and described above, a medical specialist can select an appropriately sized plate 106A in accordance with a location of the spine into which the spinal implant 100A is to be implanted and an access window to perform the spinal implant procedure.

FIGS. 7A-7H illustrate a plate 106B in accordance with a second embodiment of the present disclosure. The second embodiment illustrates a so-called "symmetric plate" in accordance with the present disclosure. Those aspects of the second embodiment of the plate 106B that are the same as the first embodiment of the plate 106A will not be repeated below.

Figure 7A:
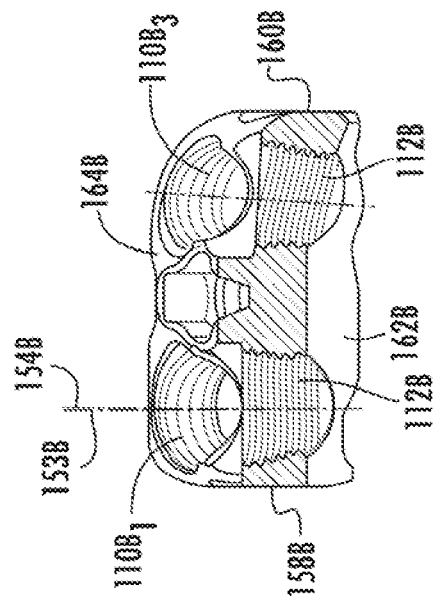
FIGS. 7A-7H illustrate a plate in accordance with a second embodiment of the present disclosure.
Figure 7B:
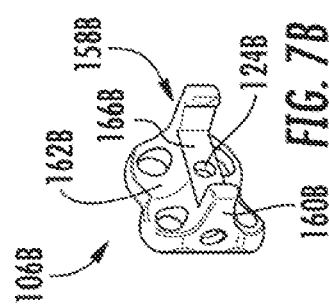

FIGS. 7A and 7B, respectively, illustrate front and rear perspective views of the plate 106B. The plate 106B includes sides 158B and 160B, a rear surface 162B and a front surface 164B. A central hole 124B is provided into which a screw (not shown) may be inserted to secure the plate 106B to the various spacer bodies described above.

Figure 7C:
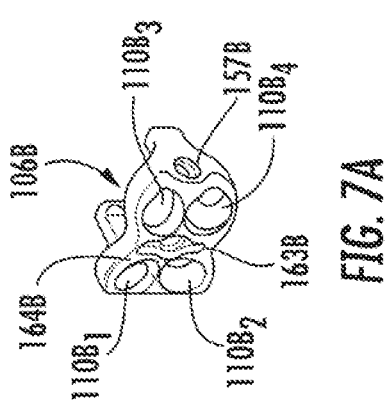
Figure 7D:
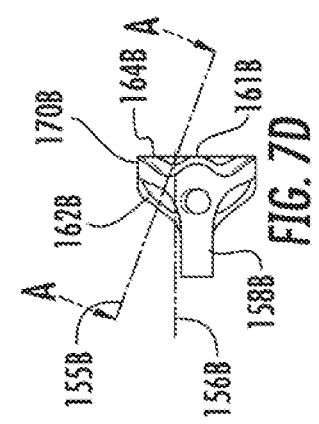

Referring now to FIG. 7C, there is shown a side view of the plate 106B showing the side 160B. The lower boreholes $110_{B2}$ and $110_{B4}$ may have a central axis 153B that is formed at an approximately 20° angle with respect to a first horizontal axis 154B passing through the center of the boreholes $110_{B2}$ and $110_{B4}$ that parallels a lateral center plane 161B of the plate 106B. As shown in the side view of FIG. 7D illustrating the side 158B, the upper boreholes $110_{B1}$ and $110_{B3}$ may have a central axis 155B that is also formed at an approximately 20° angle with respect to a second horizontal axis 156B passing through the center of the boreholes $110_{B1}$ and $110_{B3}$ that parallels the lateral center plane 161B.

Figure 14A:
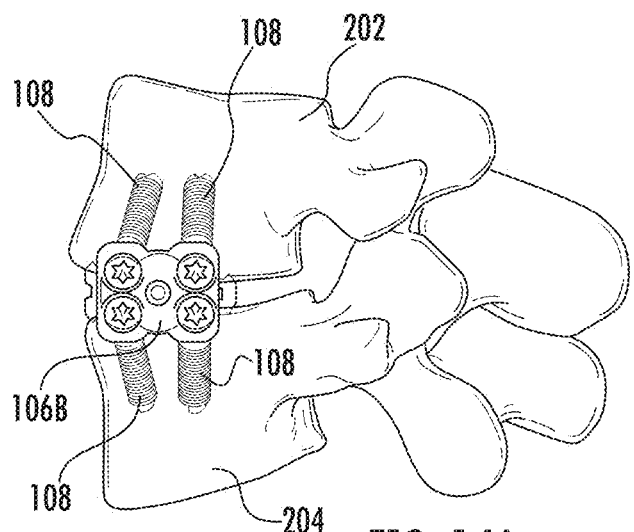
FIGS. 14A-14C, 15A-15B, 16A-16D, 17A-17C illustrate the example spinal implant, as generally positioned in the intervertebral disc space between two vertebral bodies.
Figure 14B:
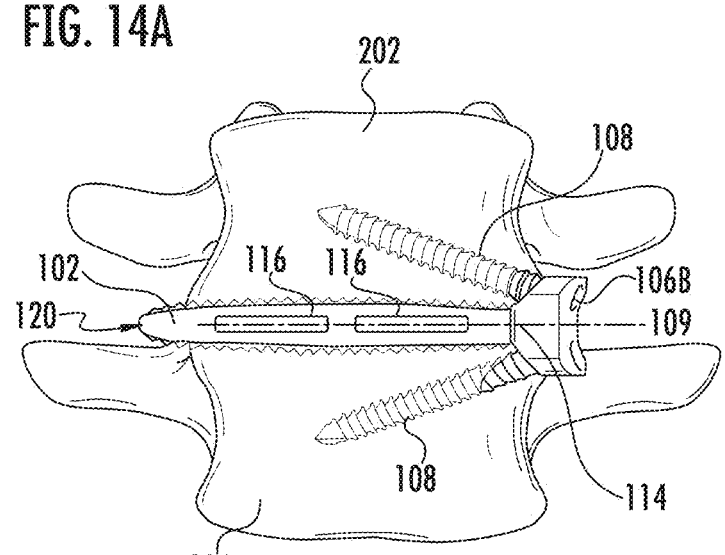

As will be shown in FIGS. 14A-14B the above offsets of the central axis causes the screws 108 inserted therein to diverge at symmetric angles about the lateral center plane 161B of the plate 106B. It is noted that central axis 153B and 155B of the lower and upper boreholes may be offset at any angle between 5° and 20° with respect to the horizontal axis 154B and 156B.

Figure 7E:
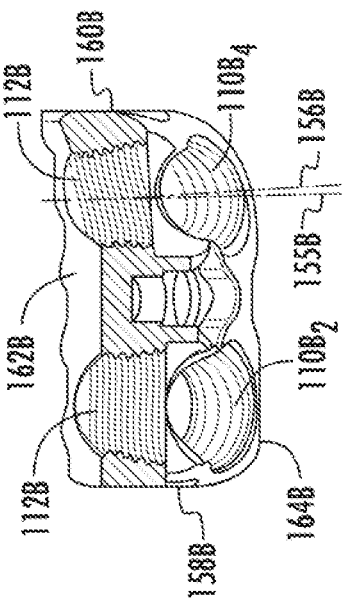
Figure 7F:
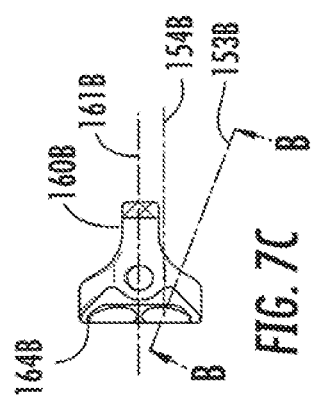
Figure 7G:
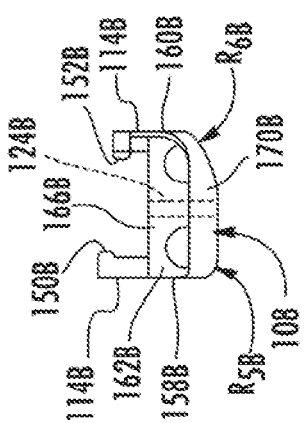
Figure 7H:
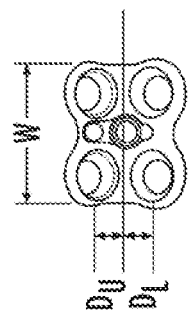

FIG. 7H illustrates a front view of the plate 106B. As illustrated, the upper boreholes $110_{B1}$ and $110_{B3}$ may be located a distance $D_U$ from the lateral center plane 161B and about the longitudinal central axis 165B. Lower boreholes $110_{B2}$ and $110_{B4}$ may be located a distance $D_L$ from a lateral center plane 161B and about the longitudinal central axis 165B. The distance $D_U$ may range from approximate 2.75 mm to 6.75 mm. Similarly, the distance $D_L$ may range from approximately 2.75 mm to 6.75 mm. Because of the symmetric shape of the plate 106B, the ratio of $D_L:D_U$ is maintained at 1, thus $D_L$ and $D_U$ are equal for all sizes of $D_L$ and $D_U$ implemented in the plate 106B. The plate 106B may have a height H that ranges from approximately 15 mm to 23 mm. The distance Q between the outer edges of the boreholes in a vertical direction may range from approximately 12 mm to 20 mm, thus providing approximately 1.5 mm of material between the outer edge of the borehole and the edge of the plate 106B. The distance U between the inner edges of the boreholes may range from approximately 0.5 mm to 8.5 mm. Also as shown in FIG. 7H, the front surface 164B defines a substantially rectangular region having dimples 176B and 178B formed along the outer edges of the plate 106B between the boreholes. The plate 106B may have a width of approximately 18 mm, as measured between the dimples formed in the sides 158B and 160B. Thus, the dimples 176B and 178B remove approximately 1 mm of material, reducing the weight of the plate 106B.

Thus, as shown in FIGS. 7A-7H and described above, a medical specialist can select an appropriately sized plate 106B in accordance with a location of the spine into which the spinal implant 100A is to be implanted and an access window to perform the spinal implant procedure.

Figure 8:
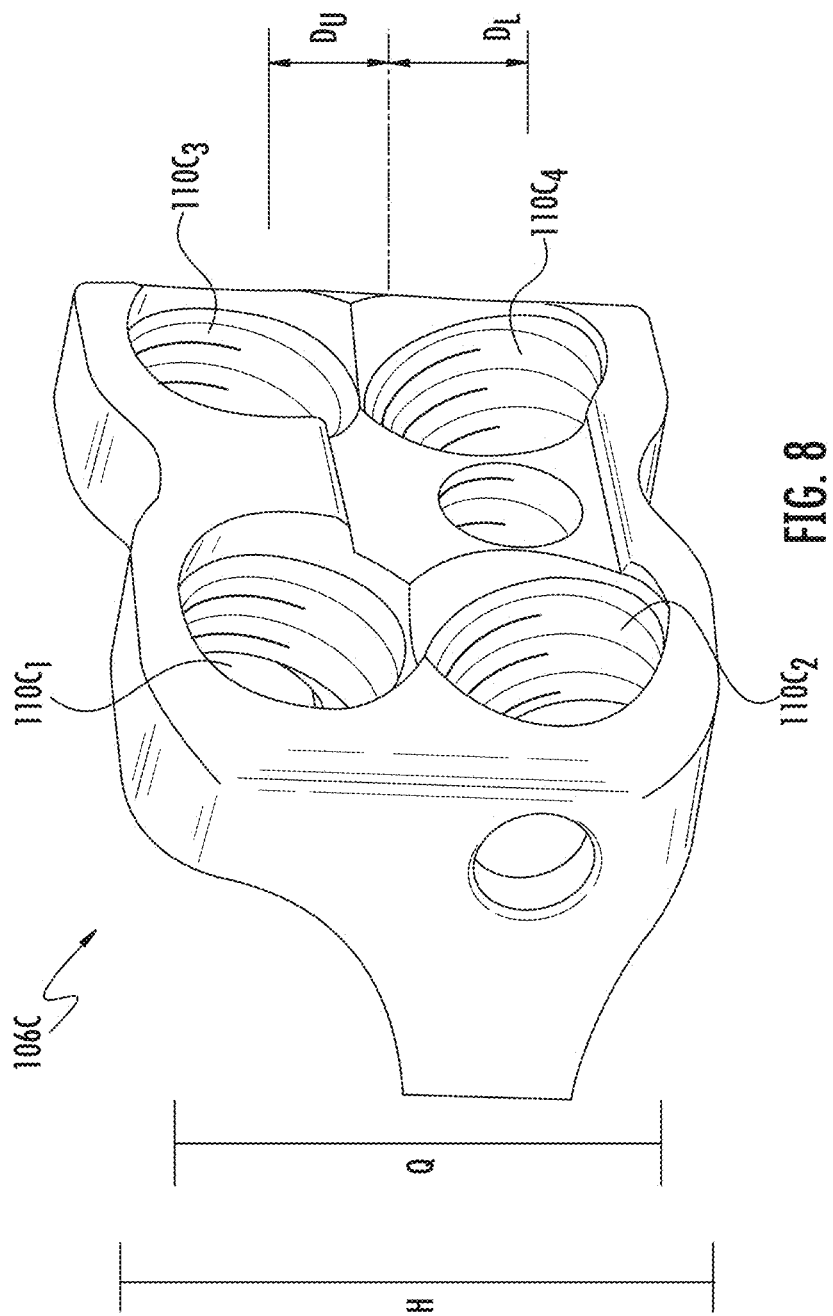
FIG. 8 illustrates a plate in accordance with a third embodiment of the present disclosure.

FIG. 8 illustrates a plate 106C in accordance with a third embodiment of the present disclosure. The plate 106C features a reduced height $D_L$ as compared to the plate 106A. For example, the height reduction may be approximately 2 mm to 4 mm. As illustrated, the upper boreholes $110_{C1}$ and $110_{C3}$ may be located a distance $D_U$ from the lateral center plane 161C. Lower boreholes $110_{C2}$ and $110_{C4}$ may be located a distance $D_L$ from a lateral center plane 161A. The distance $D_U$ may range from approximate 2.75 mm to 6.75 mm. The distance $D_L$ may range from approximately 3 mm to 7 mm. Thus, the ratio of $D_L:D_U$ is approximately 0.92 to 1.0. The plate 106C may have a height H that ranges from approximately 15 mm to 23 mm. The distance Q between the outer edges of the boreholes in a vertical direction may range from approximately 12 mm to 20 mm, thus providing approximately 1.5 mm of material between the outer edge of the borehole and the edge of the plate 106c. The distance U between the inner edges of the boreholes may range from approximately 2.5 mm to 10.5 mm. In other aspects, the plate 106C has substantially the same dimensions and features as the plate 106A.

The plate 106C enables a surgeon or any other medical professional working in the spinal region may avoid interference with the iliac crest when working near the sacrum using the assembled spinal implant having the plate 106C. The plate 106C also allows for the removal of less bone in the event that osteophyte is present. Still further, the plate 106C allows the screws 108, when inserted into the boreholes $110_{C1}$-$110_{C4}$ to penetrate bone that is closer to the disc space, thus reducing exposure of the screws 108 and lessening the risk of the screws 108 protruding into the disc space.

Figure 9:
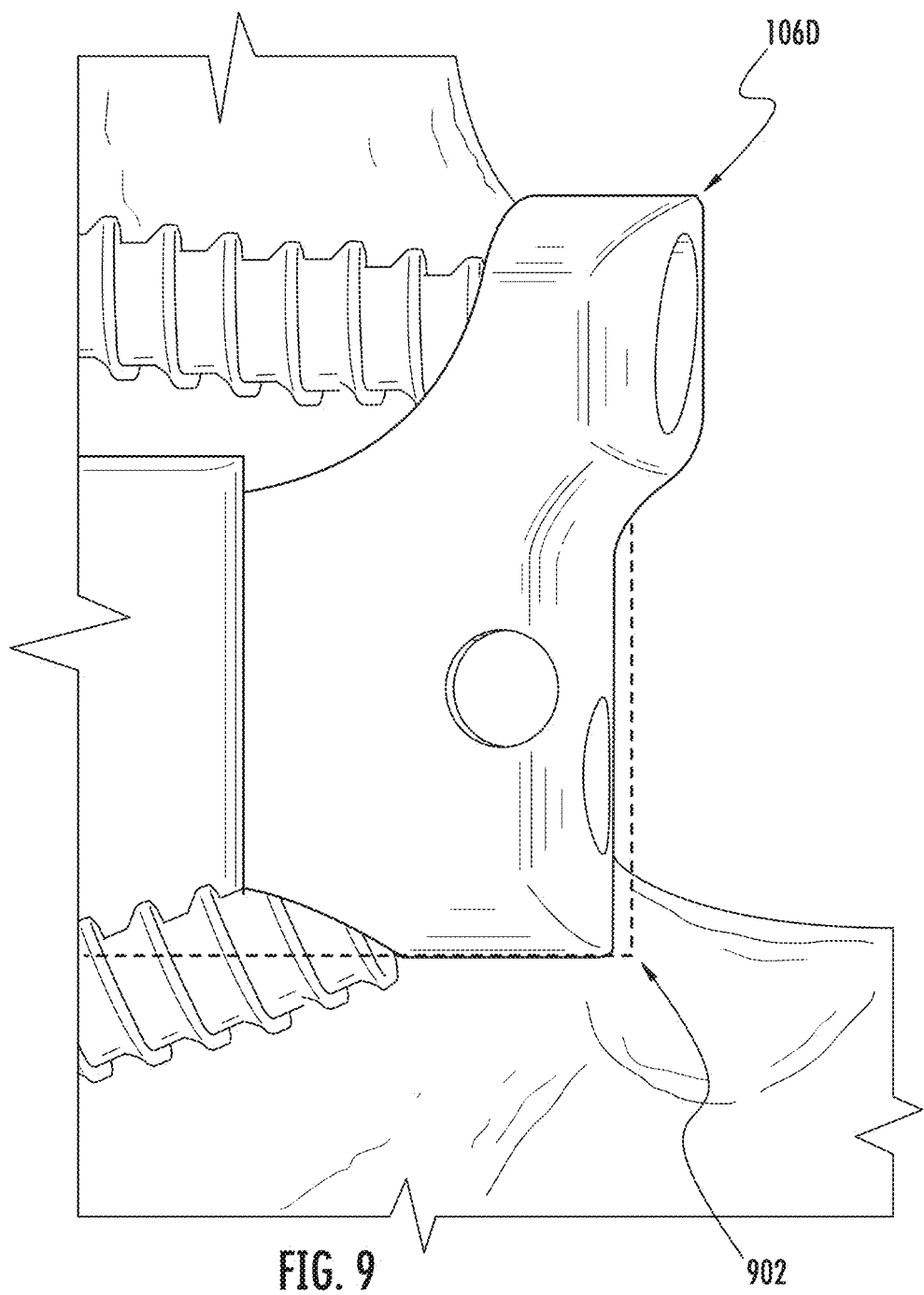
FIG. 9 illustrates a plate in accordance with a fourth embodiment of the present disclosure.

FIG. 9 illustrates a plate 106D in accordance with a fourth embodiment of the present disclosure. The plate 106D is similar to the plate 106C; however the plate 106D is configured to be mounted flush to certain portions of the anatomy in the medial-lateral plane, as well as the cranial-caudal plane. As shown, the plate 106D provides for a portion 902 in which material associated with the plate 106C that may cause irritation to a patient is removed.

Figure 10A:
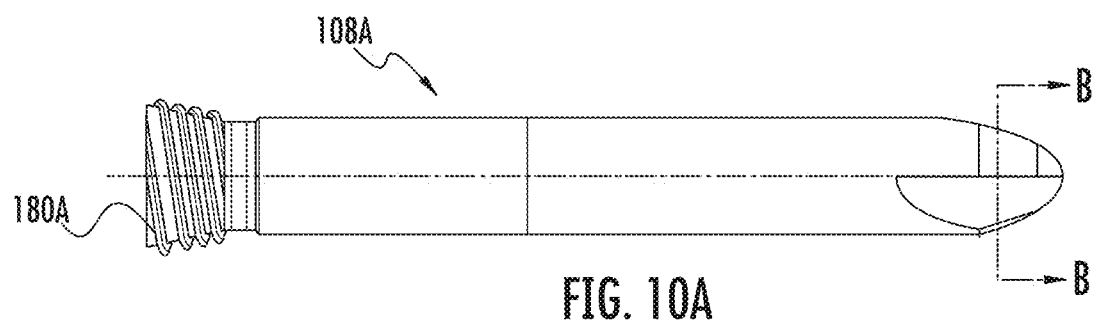
FIGS. 10A-10C illustrates a first embodiment of a screw of the present disclosure.
Figure 10B:
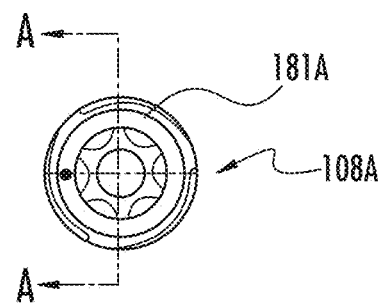
Figure 10C:
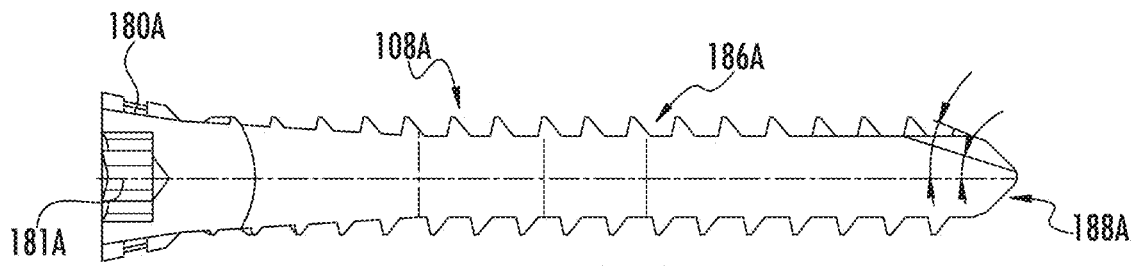

FIGS. 10A-10C illustrates a first embodiment of a screw 108A of the present disclosure. The screw 108A includes a threaded head 180A and a threaded body 186A. Thus, the threaded body 186A has relatively course pitch to provide for sufficient screw purchase into cortical bone of a vertebral body. The screw 108A has a variable angled screw point 188A where the point is initially angled at approximately 18° and then angled at approximately 22° proximate to a first thread thereof. The head of the screw 108A defines a star-shaped recess 181A, into which a complementary star-shaped driver may be inserted to drive the screw. The recess may be formed having other shapes, such as a line, a plus sign, a square or other polygon shape to receive a complementary drive. The screw 108A may have a length that may range from 20 mm to 50 mm.

Figure 11A:
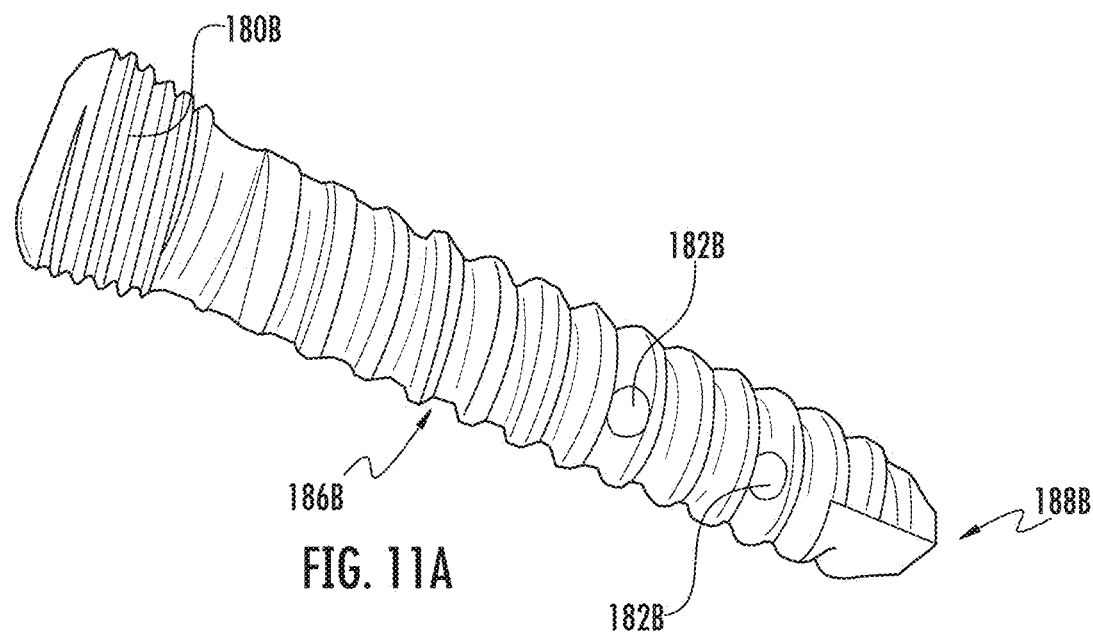
FIGS. 11A-11B illustrate a second embodiment of a screw of the present disclosure.
Figure 11B:
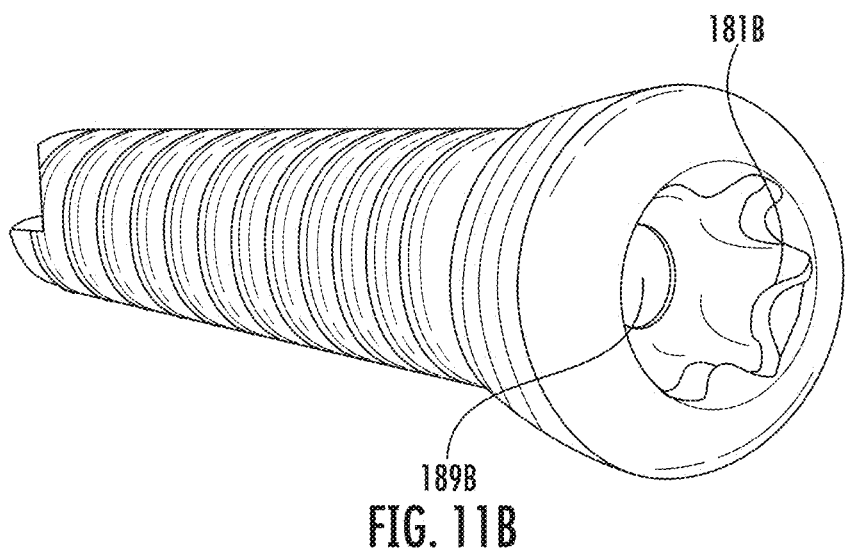

FIGS. 11A-11B illustrate a second embodiment of a screw 108B. The screw 108B shares similar features with the screw 108A in size and shape, however has a hollow center 189B into which bone cement or other adhesive may be injected. The screw 108B may be used in situations where the receiving bone is structurally unsound and may not retain the screw 108B. The screw 108B may provide for e.g., luer locking of an injection mechanism within the recess 181B. Bone cement or other adhesive may be injected into the screw 108B such that it flows within the central hollow region 189B of the screw 108B and out of the holes 182B into the threads and surrounding bone to secure the screw 108B within, e.g., a vertebral body.

Figure 12A:
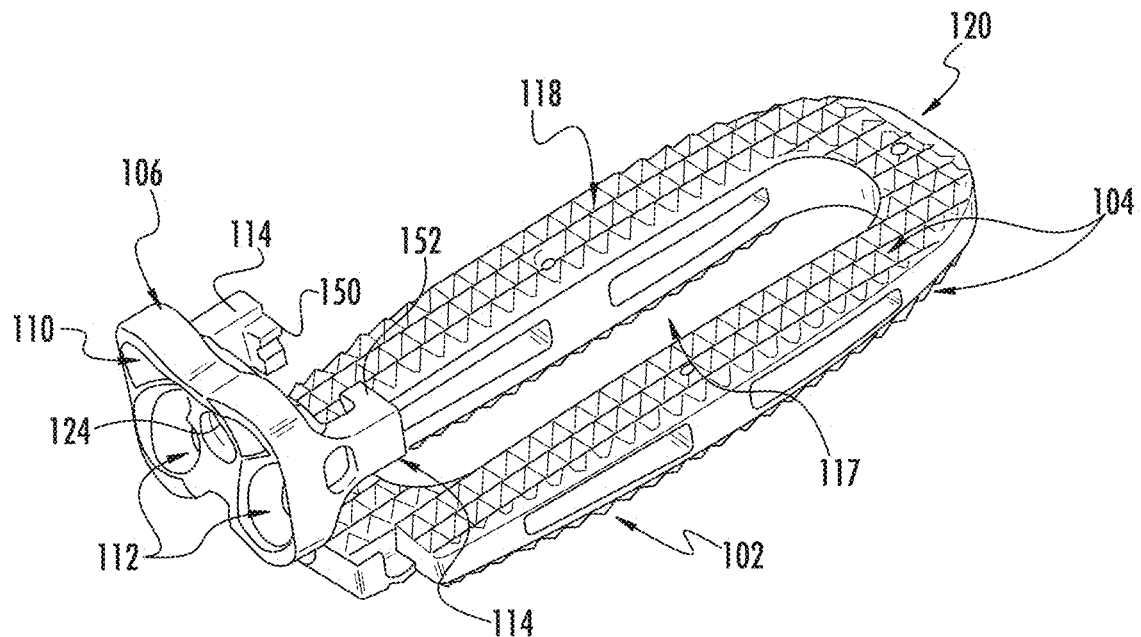
FIGS. 12A-12B illustrate an example sequence of assembly of the spinal implant of FIG. 1.
Figure 12B:
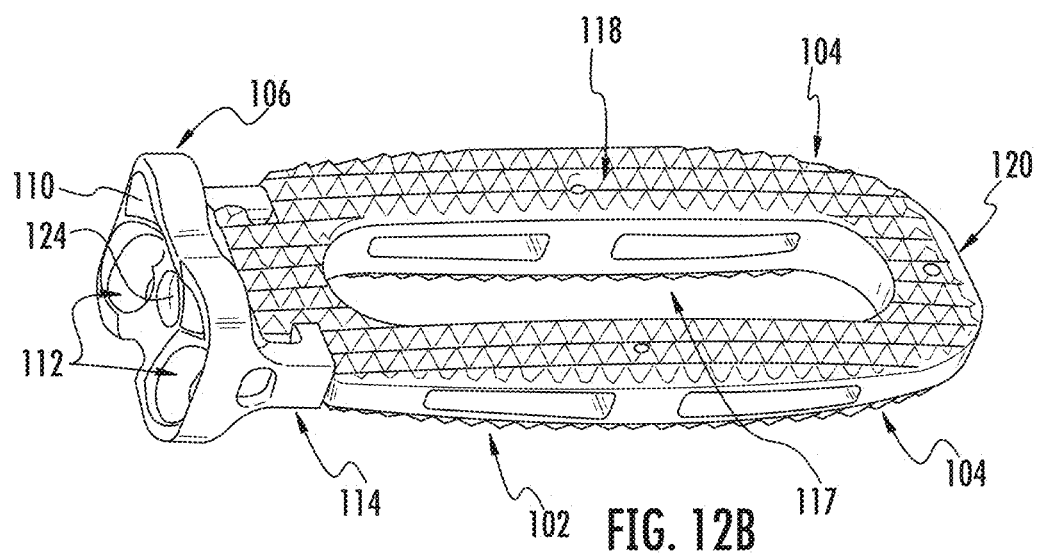

Referring now to FIGS. 12A-12B, there is shown an example sequence of assembly of the spinal implant 100A using, e.g., spacer body 102C and plate 106B. As illustrated, the plate 106B and the spacer body 102C are cooperatively configured to mate with one another. In the sequence of FIGS. 12A-12B the coupling flanges 114 are pressed into the recesses 140A defined in the sides 130A and 132A to receive the inward pointing projections 150B and 152B of the coupling flanges 114 in order to snap the plate 106B securely into place on the spacer body 102C. Thus, the spinal implant 100A is ready for use by a medical specialist as part of a spinal repair procedure.

Figure 13:
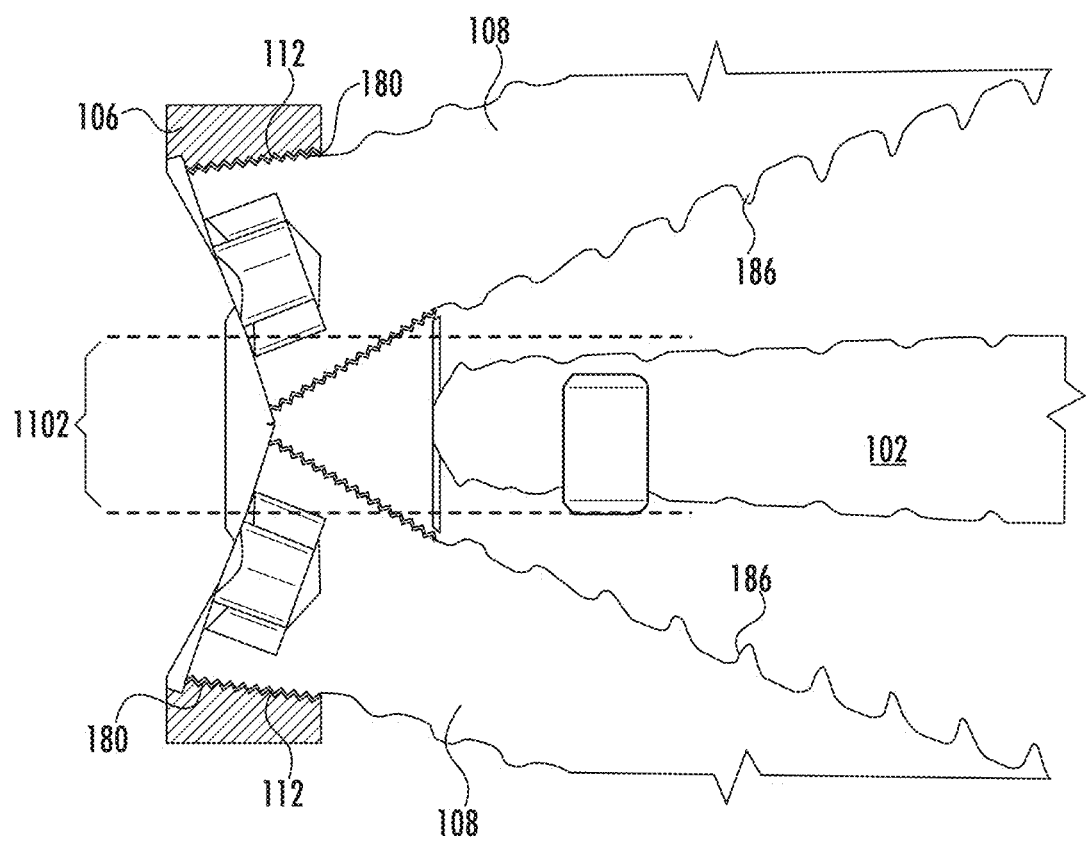
FIG. 13 illustrates the assembled spinal implant of FIG. 1, together with screws inserted therein.

Referring now to FIG. 13, there is illustrated the assembled spinal implant 100A together with screws 108 inserted therein. As illustrated in FIG. 13, the inserted screw heads are partially contained within a space 1102 defined by the height of the spacer 102 between the top surface 134 and the bottom surface 136. Such an arrangement provides for a more compact access window area as the screws are position closer together in a vertical orientation. In accordance with aspects of the present disclosure, the engagement of the threaded head 180 and the locking threads 112 fixes the angles of the screws 108 with respect to the plate 106.

As will now be described with reference to FIGS. 14-18, the spinal implant 100 may be laterally inserted into an intervertebral space between two vertebral bodies. For example, the spinal implant 100 may be used to impart superior stability to a lytic spondylolisthesis or provide structural stability in skeletally mature individuals following discectomies. Embodiments of the present disclosure may be used for work in, around, or within the lumbar sections L1 to L4 or thoracic sections T9 to T12. Alternatively, the implant 100 (of varying length to width ratios) may be implanted anteriorly into an intervertebral space between two vertebral bodies.

Figure 14C:
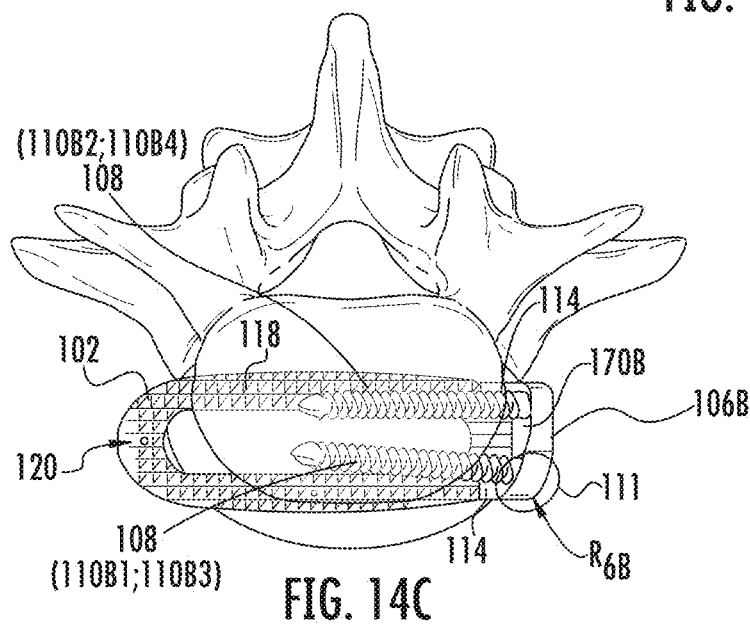

Referring now to FIGS. 14A-14C, there is illustrated an example spinal implant as generally positioned in the intervertebral disc space between two vertebral bodies 202 and 204. The spinal implant 100A may include any of the spacer bodies 102A-102D and the plate 106B, thus providing a symmetric divergence of the screws 108. The boreholes $110_{B1}$-$110_{B4}$ of the plate 106 are located near the corners of the plate 106B, thus positioning the screws 108 to coincide with the portion of the vertebral bodies 202 and 204 that is strongest. The corner portion of the plate 106 aligns with the Cortical Rim, thus providing a sufficient amount of cortical bone for the screws 108 to engage to retain the implant 100 in a desired position.

As shown in FIG. 14B, the upper screws 108 and lower screws 108 diverge at a symmetric angle from a midline 109 of the implant 100. As noted above, where the screws 108 diverge symmetrically from the midline 109, the screws may diverge at an angle between 10° and 30° for a lateral approach and between 20° and 45° for an anterior approach with respect to the centerline 109. As shown in FIG. 14C, the anterior screw may angle posteriorly at an angle that is approximately 0° and 3° and the posterior screw may angle anteriorly at an angle which may be approximately 0° and 3°, as illustrated in FIGS. 7E and 7F and discussed in detail with regard to FIGS. 6E and 6F and boreholes $110_{B1}$-$110_{B4}$. The divergent angles of the screws are fixed because of the aforementioned engagement of the screw head 180 and locking threads 112, thus increasing the stability of the spinal implant 100 within the body, while avoiding any concerns of the ends of the screws 108 penetrating the wall of the vertebral body 202 or 204 from the inside out.

Also shown in FIG. 14C, the top surface 170B of the plate 106 is generally medially curved such that it substantially matches a curvature an outer wall of a superior vertebral body. A similar curved region is formed from the side the bottom of the plate 106 that substantially matches a curvature an outer wall of an inferior vertebral body. Thus, the plate 106 achieves a better fit with the outer surface of vertebral bodies. For example, the curvature of the plate 106 reduces or eliminates any gap that may exist between the rear surface 162 of the plate 106 and an outer wall of the vertebral bodies 202 and 204, thus providing more stability (see, region 111).

Figure 15A:
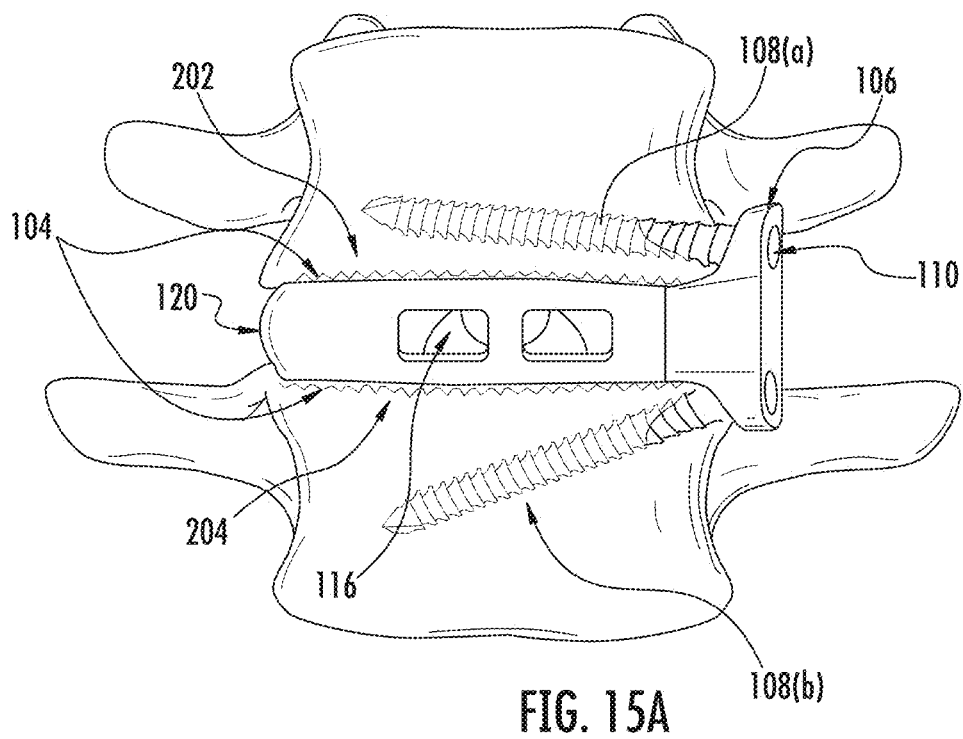
Figure 15B:
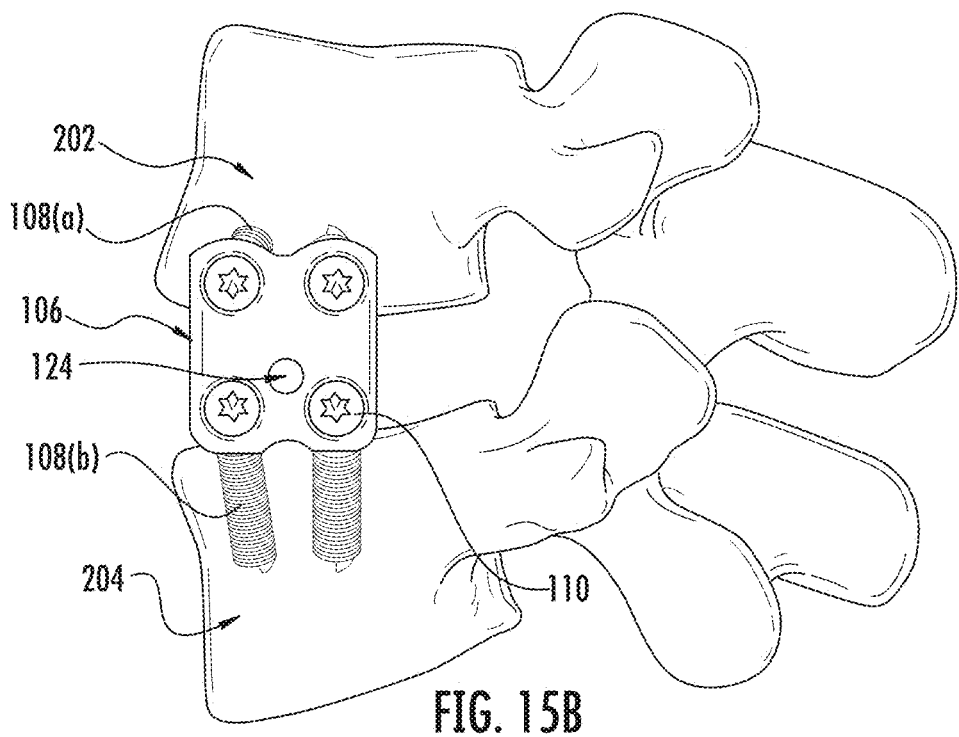

Referring now to FIGS. 15A-15B, there is illustrated the spinal implant 100A as implanted between two vertebral bodies. The spinal implant 100A may include any of the spacer bodies 102A-102D and the plate 106A, thus providing an asymmetric divergence of the screws 108. As illustrated, upper screws 108 and lower screws 108 diverge at an asymmetric angle from a midline 109 of the implant 100. As shown, the upper screws 108(a) may diverge at an angle between 0° and 10° with respect to the centerline 109, whereas the lower screws 108(b) may diverge at an angle between 10° and 30° with respect to the centerline 109. The implementation of FIGS. 15A-15B is useful when working near the iliac crest because the 'flatness' or small angle of the upper screws 108 does not interfere with the iliac crest. Although not shown, the anterior screw may angle posteriorly and the posterior screw may angle anteriorly, as discussed above with regard to FIG. 14C.

Figure 16A:
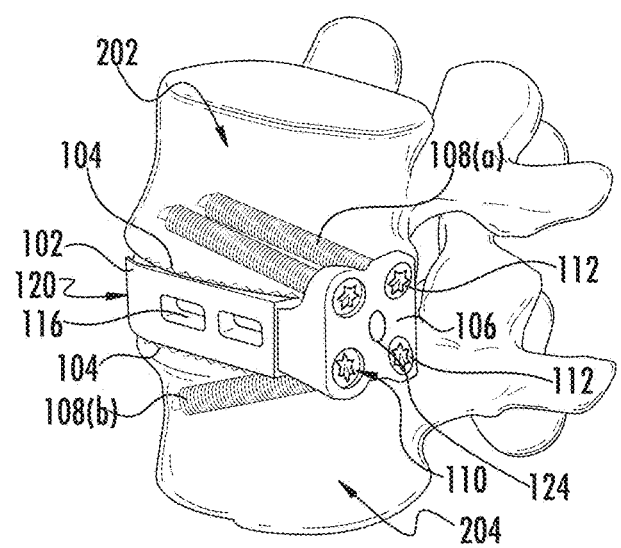
Figure 16B:
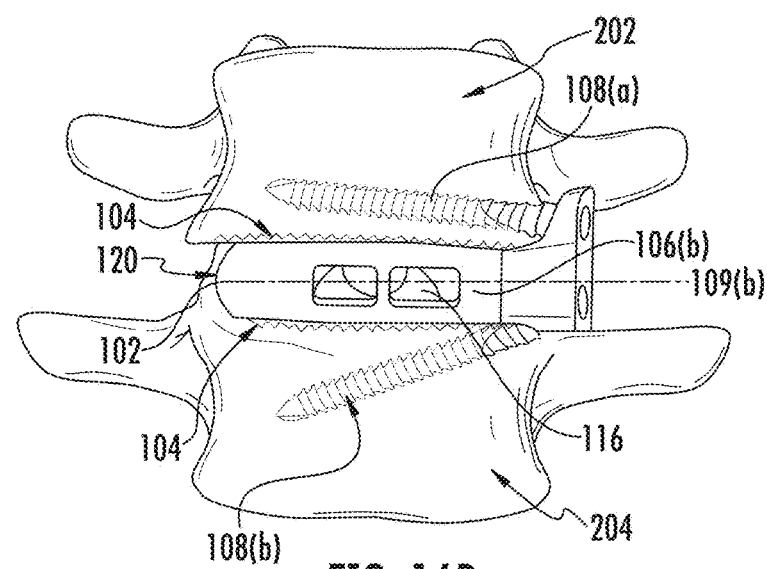
Figure 16C:
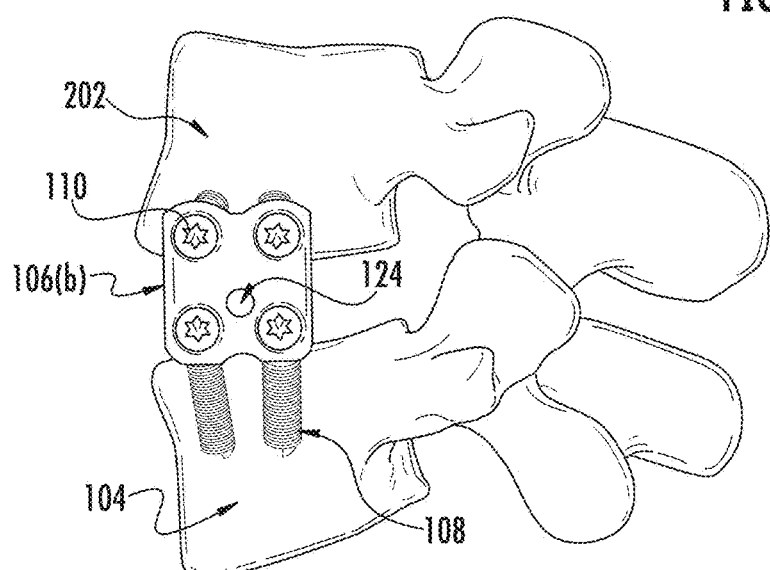

FIGS. 16A-16D illustrate an example spinal implant as generally positioned in the intervertebral disc space between two vertebral bodies 202 and 204. For example, the spinal implant 100 shown in FIGS. 16A-16D may be used when working in lumbar or thoracic section of the spine. The spinal implant 100 may include any of the spacer bodies 102A-102D, as modified (see discussion with reference to FIG. 16D below) and the plate 106C, thus providing an asymmetric divergence of the screws 108. As shown in FIG. 16B, the upper screws 108 and lower screws 108 diverge at an asymmetric angle from a midline 109 of the implant 100. As shown, the upper screws 108(a) may diverge at an angle between 0° and 10° with respect to the centerline 109, whereas the lower screws 108(b) may diverge at an angle between 10° and 30° with respect to the centerline 109. Although not shown, the anterior screw may angle posteriorly and the posterior screw may angle anteriorly, as discussed above with regard to FIG. 14C.

Figure 16D:
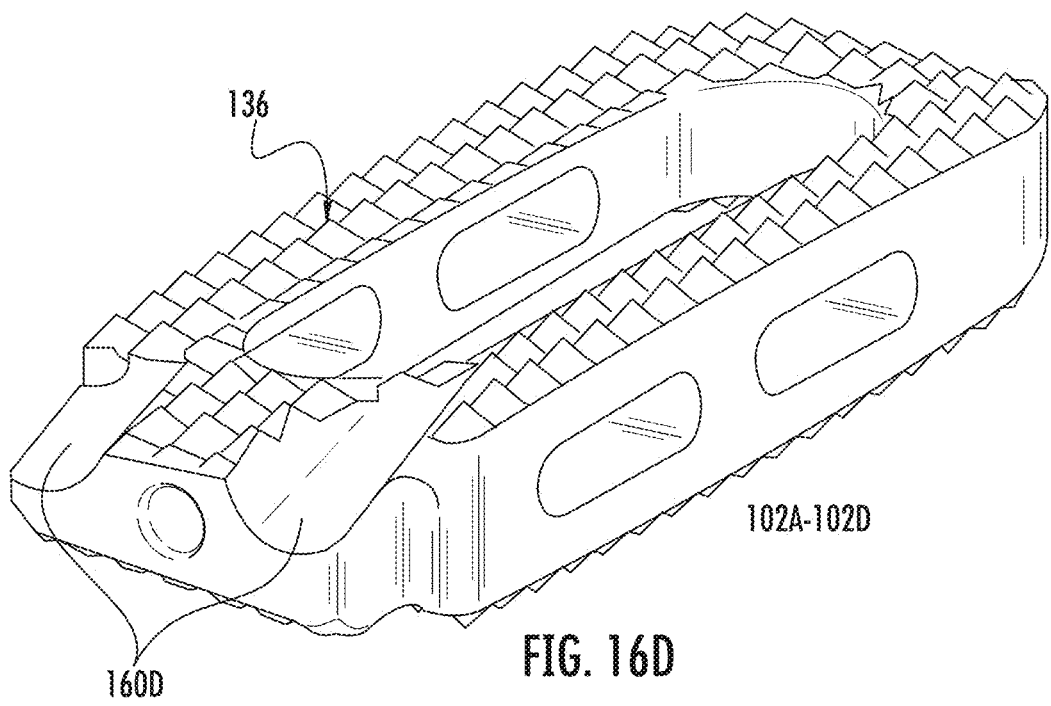

As shown in FIG. 16D, to provide the height reduction of the plate 106C described in FIG. 8, the bottom surfaces 136A-136D of the spacer bodies 102A-102D may be modified to define guide grooves 1600 that align with the boreholes $110_{C2}$ and $110_{C4}$ of the plate 106C. As such, when the screw 108 is inserted into the boreholes $110_{C2}$ or $110_{C4}$, the screw will pass through an interior of the boreholes $110_{C2}$ or $110_{C4}$ and through the guide groove 1600 before penetrating into the cortical bone of the vertebral body (e.g., vertebral bodies 202 and 204).

The spinal implant 100 including the plate 106C enables a surgeon or any other medical professional working in the spinal region may avoid interference with the iliac crest when working near the sacrum using the assembled spinal implant having the plate 106C. The plate 106C also allows for the removal of less bone in the event that osteophyte is present.

Figure 17A:
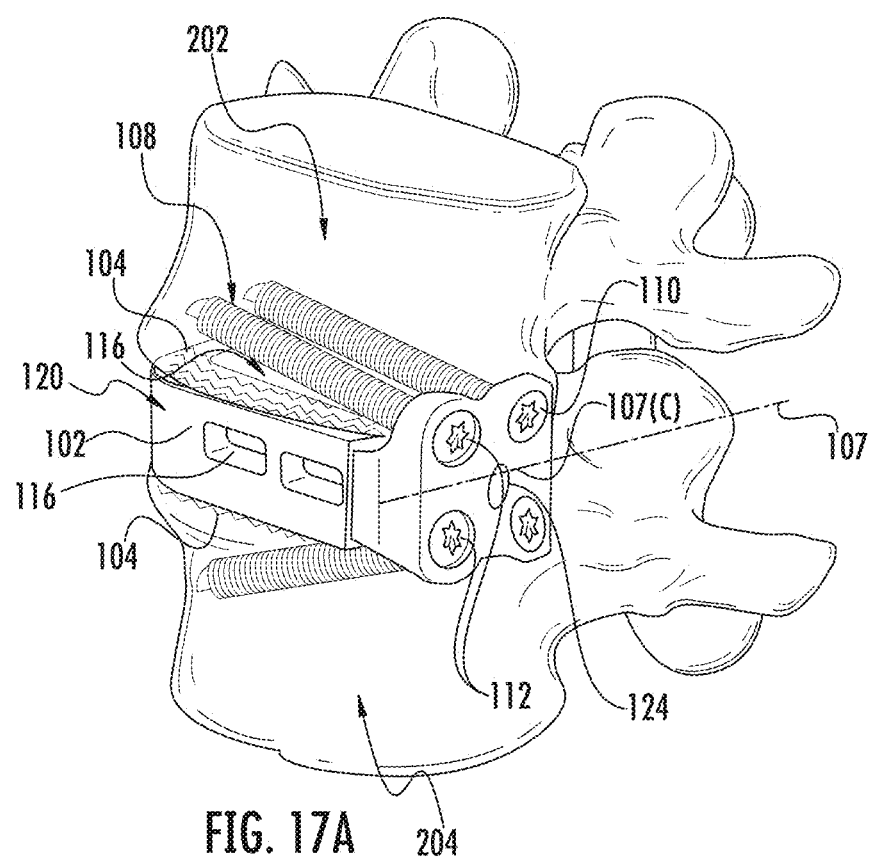
Figure 17C:
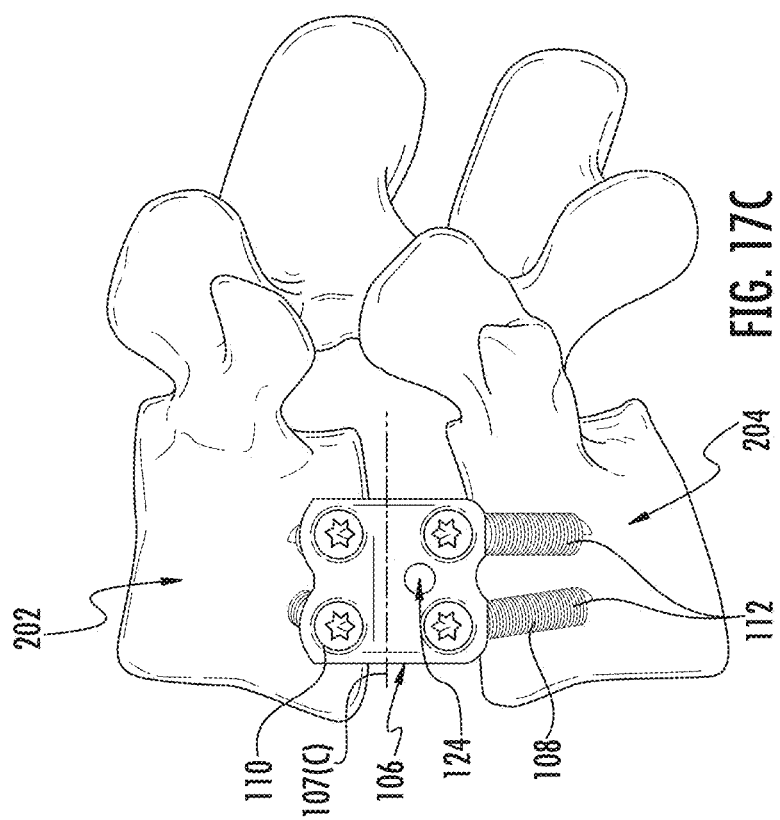
Figure 17B:
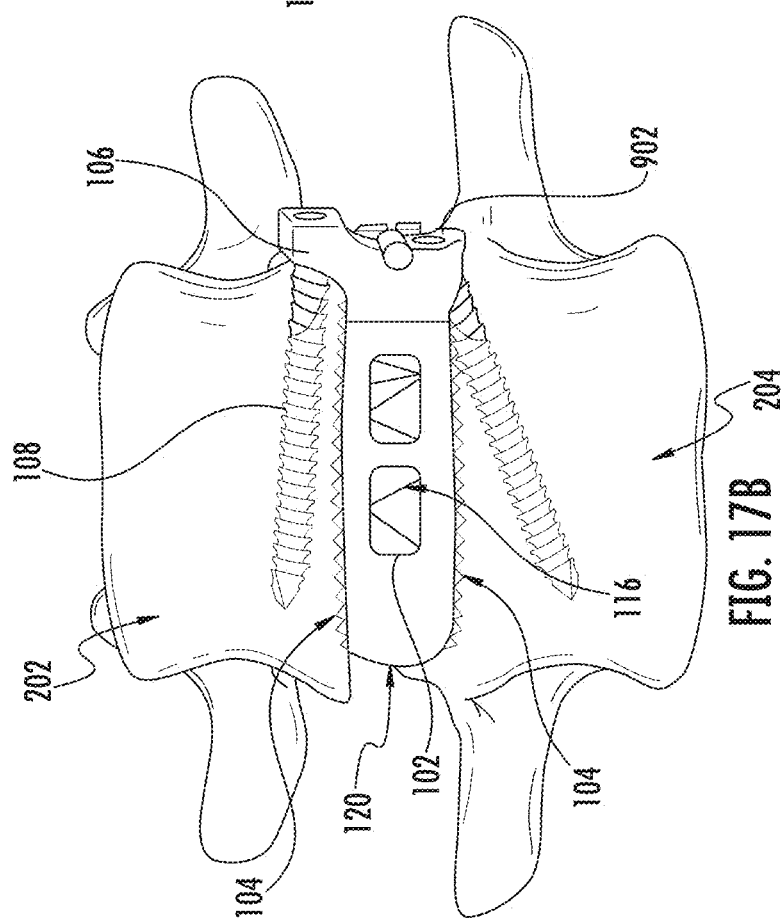

FIGS. 17A-17C illustrate another example spinal implant as generally positioned in the intervertebral disc space between two vertebral bodies 202 and 204. The spinal implant 100 may include any of the spacer bodies 102A-102D, as modified in FIG. 16D, and the plate 106D, thus providing an asymmetric divergence of the screws 108. As shown in FIG. 17B, the upper screws 108 and the lower screws 108 diverge at an asymmetric angle from a midline 109 of the implant 100. As shown, the upper screws 108(a)

may diverge at an angle between 0° and 10° with respect to the centerline 109, whereas the lower screws 108(b) may diverge at an angle between 10° and 30° with respect to the centerline 109. Although not shown, the anterior screw may angle posteriorly and the posterior screw may angle anteriorly, as discussed above with regard to FIG. 14C.

In the example of FIGS. 17A-17C, the spinal implant 100, and in particular, the plate 106D is optionally configured to be mounted flush to certain portions of the anatomy in the medial-lateral plane, as well as the cranial-caudal plane. As shown, the plate 106D provides for a portion 902 in which material associated with the plate 106D is removed.

Figure 18A:
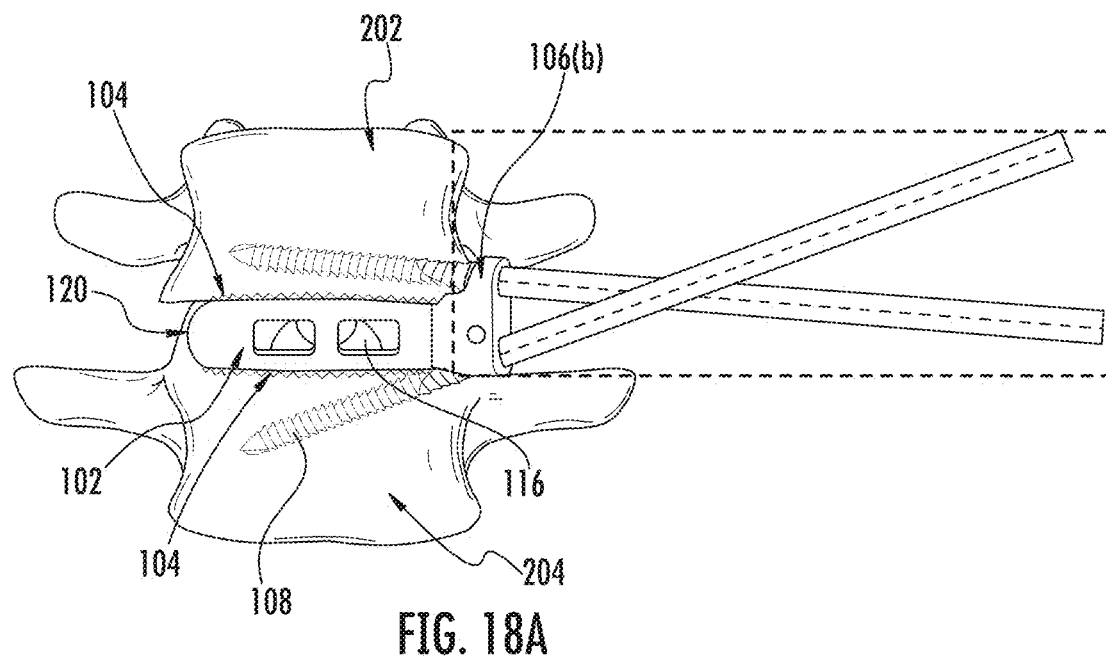
FIGS. 18A-18B illustrate a comparison of access windows during a spinal implant procedure using various plates of the present disclosure.
Figure 18B:
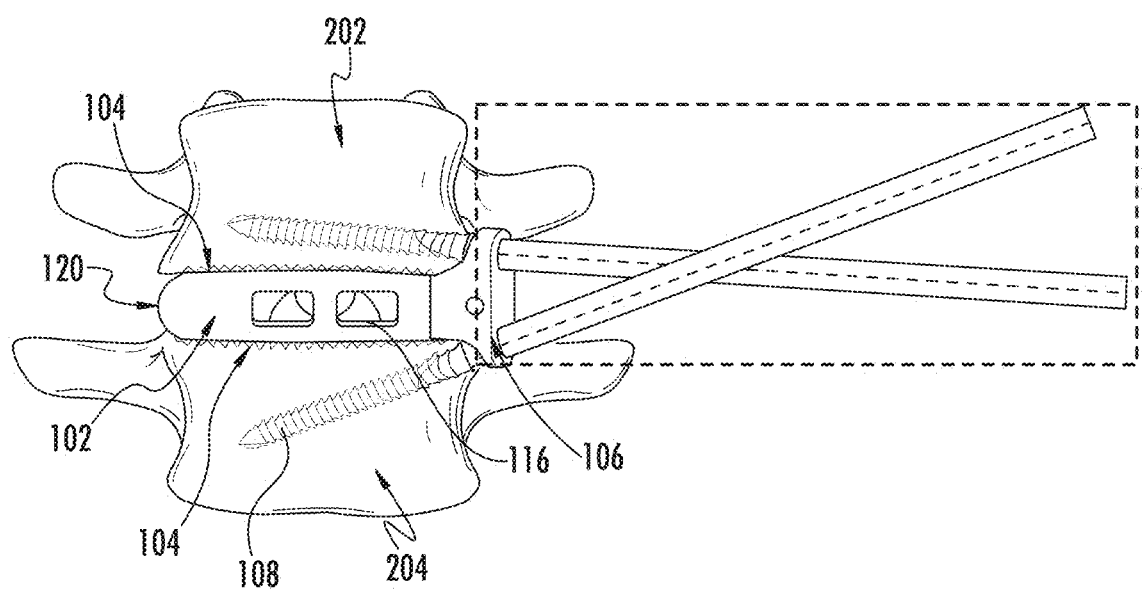

Referring to FIGS. 18A-18B, there is illustrated a comparison of access windows that may be opened during a spinal implant procedure. FIG. 18A illustrates the access window when one of plates 106C or 106D are utilized. The spinal implant 100 allows for an equivalent access window when the placement of screws 108 is carried out through 0°. As shown, the plate 106C or 106D has an approximately 1 mm-2 mm overhang with respect to the outer wall of the vertebral body 202. However, there is no overhang with respect to the vertebral body 204. In FIG. 18B, in contrast, illustrates the spinal implant using the plate 106A. The access window in FIG. 18B, is slightly larger to accommodate insertion of the screws 108 through the boreholes in the slightly larger plate 106A.

Figure 19A:
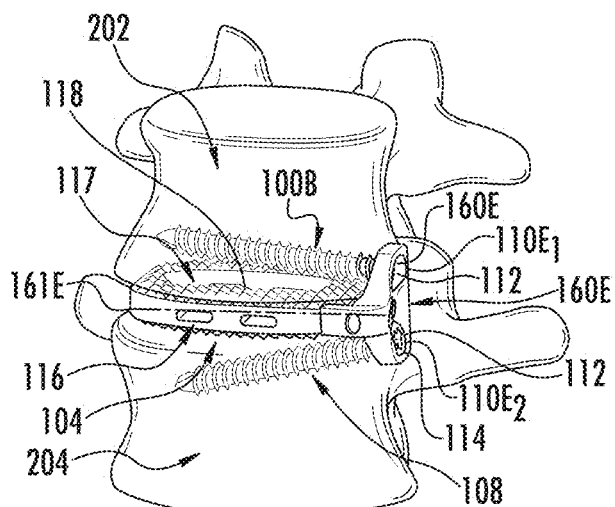
FIGS. 19A-19C illustrate another spinal implant of the present disclosure.
Figure 19B:
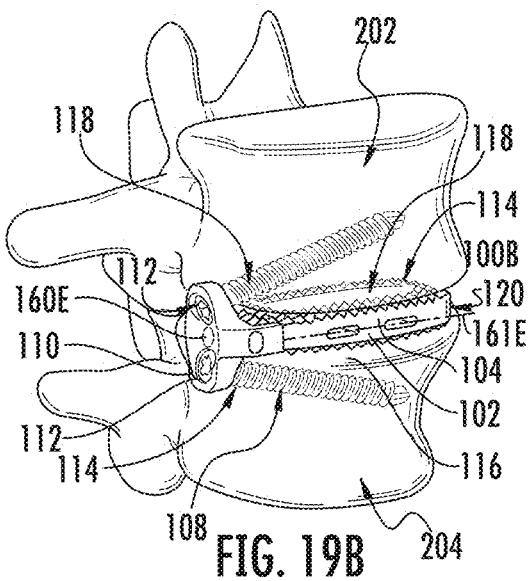
Figure 19C:
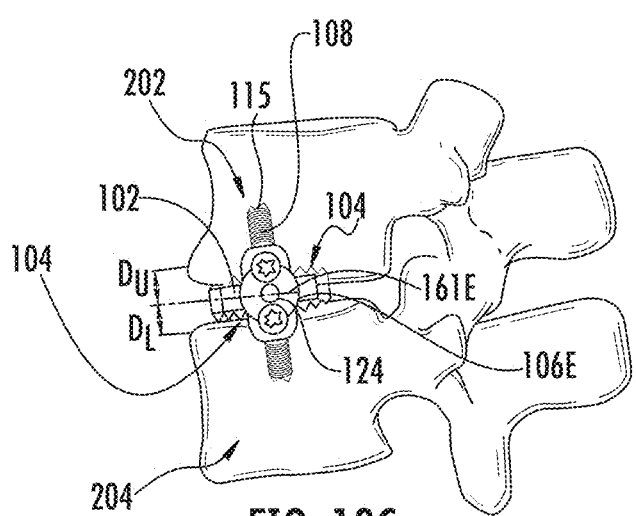

FIGS. 19A-19C illustrate another spinal implant 100B of the present disclosure. The spinal implant 100B is depicted in which the boreholes 110 and screws 108 are aligned along the midline 125 of a plate 106E in accordance with a fifth embodiment. The centralized location of the boreholes 110 and screws 108 presents less risk of the screws 108 breaking through the anterior cortex, thus reducing the likelihood of causing vessel damage. In FIG. 19A, there is shown a side view of the plate 106E showing a side 160E. The lower borehole $110_{E2}$ may be formed at an approximately 20° angle with respect to a lateral center plane 161E of the plate 106E. The upper borehole $110_{E1}$ may be formed at an approximately 20° angle with respect to the lateral center plane 161E.

In the front view of FIG. 19C, the upper borehole $110_{E1}$ may be located a distance $D_U$ from the lateral center plane 161E. The lower borehole $110_{E2}$ may be located a distance $D_L$ from a lateral center plane 161E. The distance $D_U$ may range from approximate 2.75 mm to 6.75 mm. Similarly, the distance $D_L$ may range from approximately 2.75 mm to 6.75 mm. Because of the symmetric shape of the plate 106E, the ratio of $D_L:D_U$ is maintained at 1, thus $D_L$ and $D_U$ are equal for all sizes of $D_L$ and $D_U$ implemented in the plate 106E. The plate 106E may have a height H that ranges from approximately 15 mm to 23 mm. The distance Q between the outer edges of the boreholes in a vertical direction may range from approximately 12 mm to 20 mm, thus providing approximately 1.5 mm of material between the outer edge of the borehole and the edge of the plate 106E. The distance U between the inner edges of the boreholes may range from approximately 0.5 mm to 8.5 mm.

As shown in FIG. 19B, the above offsets of the central axis causes the screws 108 inserted therein to diverge at symmetric angles about the lateral center plane 161E of the plate 106E. It is noted that central axis 153E and 155E of the lower and upper boreholes may be offset at any angle between 5° and 20° with respect to the horizontal axis 154E and 156E. Although not shown, the plate 106E may provide for asymmetric divergence of the screws, as described with regard to the plate 106A. Other aspects of the plate 106E may be similar to the plate 106A, for example, the rear surface of the plate 106E may be curved to provide a better fit with the outer walls of the vertebral bodies 202 and 204.

Figure 20:
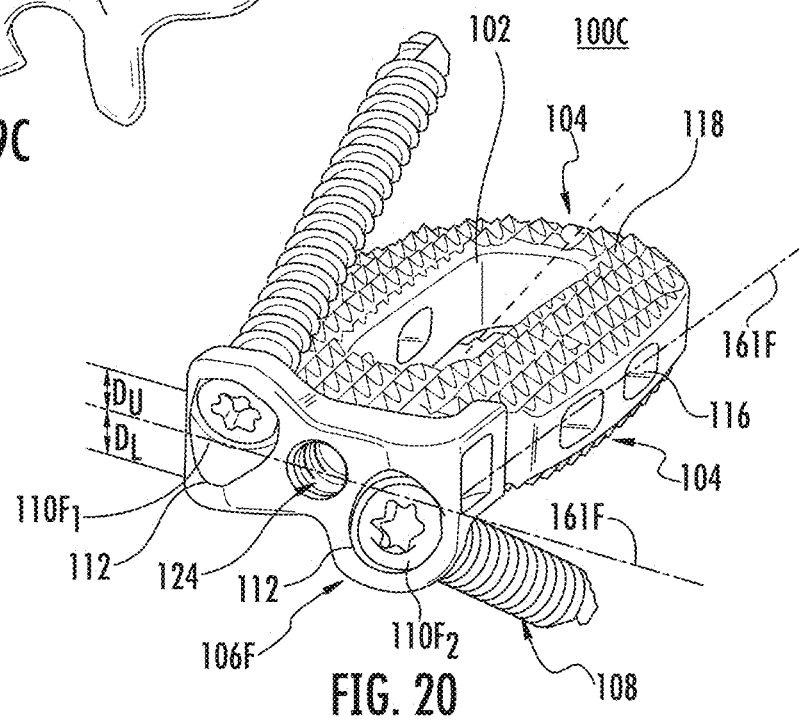
FIG. 20 illustrates another spinal implant of the present disclosure.

Referring now to FIG. 20, there is illustrated another spinal implant 100C having a plate 106F in accordance with a sixth embodiment to provide for alternative screw positions. The spinal implant 100C allows the surgeon or medical professional to minimize the opening required for placement of the screws 108, as the plate 106F comprises boreholes 110 that are proximate to a centerline 107F of the plate 106F.

In particular, the plate 106F may be configured similarly as the plate 106B with boreholes $110_{B2}$ and $110_{B3}$ removed from the plate 106B. The lower borehole $110_{F2}$ may be formed at an approximately 20° angle with respect to a lateral center plane 161F of the plate 106F. The upper borehole $110_{F1}$ may be formed at an approximately 20° angle with respect to the lateral center plane 161F. This causes the screws 108 inserted therein to diverge at symmetric angles about the lateral center plane 161F of the plate 106F. It is noted that central axis 153F and 155F of the lower and upper boreholes may be offset at any angle between 5° and 20° with respect to the horizontal axis 154F and 156F. Although not shown, the plate 106F may provide for asymmetric divergence of the screws, as described with regard to the plate 106A.

The upper borehole $110_{F1}$ may be located a distance $D_U$ from the lateral center plane 161F. The lower boreholes $110_{F2}$ may be located a distance $D_L$ from a lateral center plane 161F. The distance $D_U$ may range from approximate 2.75 mm to 6.75 mm. Similarly, the distance $D_L$ may range from approximately 2.75 mm to 6.75 mm. Because of the symmetric shape of the plate 106B, the ratio of $D_L:D_U$ is maintained at 1, thus $D_L$ and $D_U$ are equal for all sizes of $D_L$ and $D_U$ implemented in the plate 106F. The plate 106F may have a height H that ranges from approximately 15 mm to 23 mm. The distance Q between the outer edges of the boreholes in a vertical direction may range from approximately 12 mm to 20 mm, thus providing approximately 1.5 mm of material between the outer edge of the borehole and the edge of the plate 106B. The distance U between the inner edges of the boreholes may range from approximately 0.5 mm to 8.5 mm. Optionally, the boreholes $110_{F2}$ and $110_{F2}$ of plate 106F may be configured to enable the anterior screw to angle posteriorly, while and the posterior screw's trajectory may be straight or angled anteriorly.

FIGS. 21A-21D illustrate another spinal implant 100D having a plate 106G in accordance with a seventh embodiment the present disclosure. The plate 106G is configured to enable the use of three screws 108 with the spinal implant 100G when inserted into an intervertebral space between two vertebral bodies. The plate 106G may be configured with two upper boreholes $110_{G1}$ and $110_{G3}$ and a lower borehole $110_{G2}$. As show in FIGS. 21A and 21C, the upper boreholes may have similar characteristics as boreholes $110_{G1}$ and $110_{G3}$. In particular, the upper boreholes $110_{G1}$ and $110_{G3}$ may be formed having an approximately 5° angle with respect to the lateral center plane 161G. The lower borehole $110_{G2}$ may be formed having an approximately 20° angle with respect the lateral center plane 161G of the plate 106G. As show in FIG. 21B, the upper boreholes $110_{G1}$ and $110_{G3}$ may be formed having an approximately 20° angle with respect to the lateral center plane 161G. The lower borehole $110_{G2}$ may be formed having an approximately 20° angle with respect the lateral center plane 161G of the plate 106G.

Figure 21A:
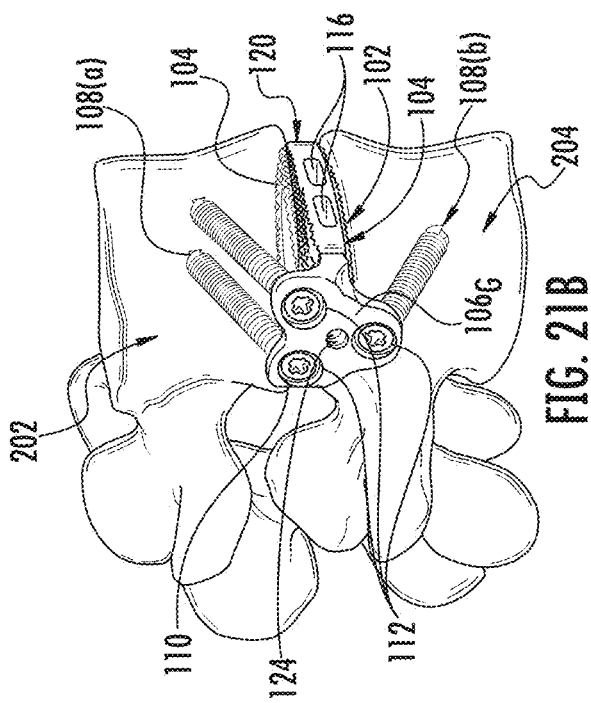
FIGS. 21A-21D illustrate another spinal implant of the present disclosure.
Figure 21B:
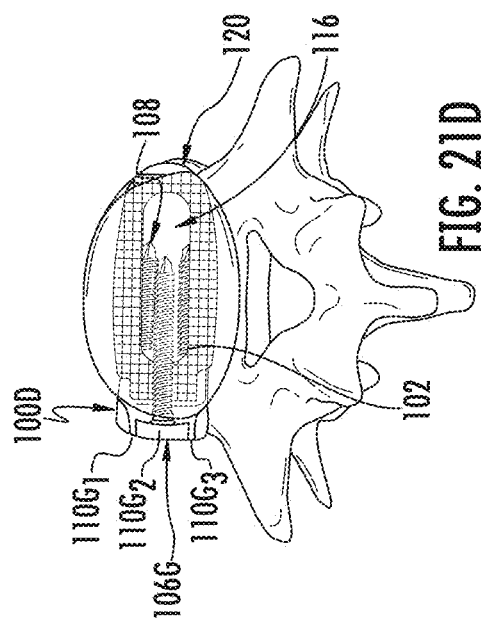
Figure 21C:
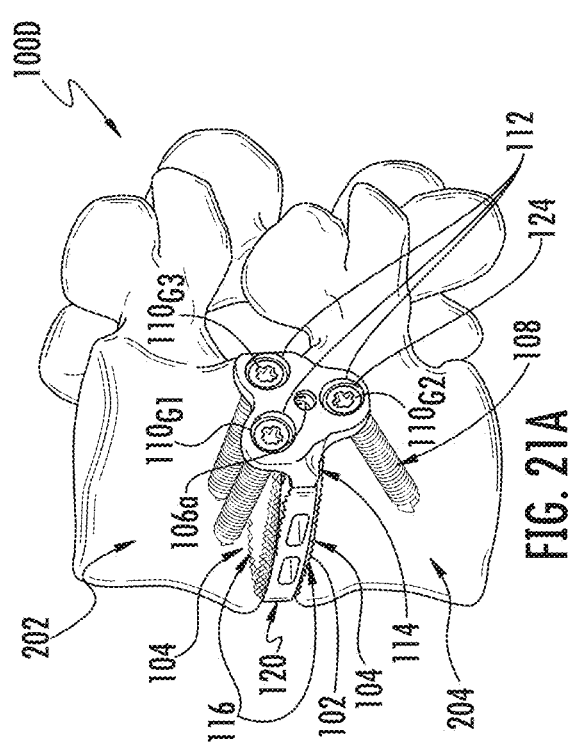

As shown in FIGS. 21A and 21C, the above offsets of the central longitudinal plant causes the screws 108 inserted therein to diverge at asymmetric angles about the lateral center plane 161G of the plate 106G, whereas in FIG. 21B the screws 108 inserted therein to diverge at symmetric angles about the lateral center plane 161G of the plate 106G. It is noted that the lower and upper boreholes may be offset at any angle between 5° and 20° with respect to the lateral center plane 161G.

Figure 21D:
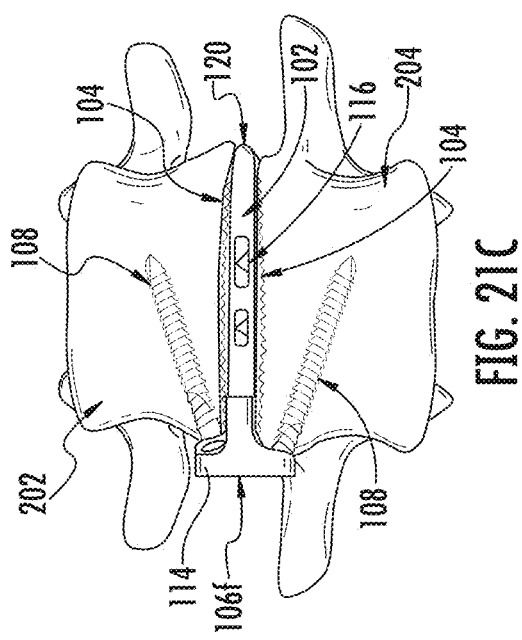

As shown in FIG. 21D, in accordance with the discussion of FIG. 14C, the upper borehole 110$_{G1}$ may be formed such that it is laterally offset at approximately a 3° angle. The upper boreholes 110$_{G3}$ may be formed having a laterally offset at approximately a 1° angle. The divergence of the screws inserted into the boreholes 110$_{G1}$ and 110$_{G3}$ is shown in FIG. 21D.

Figure 22B:
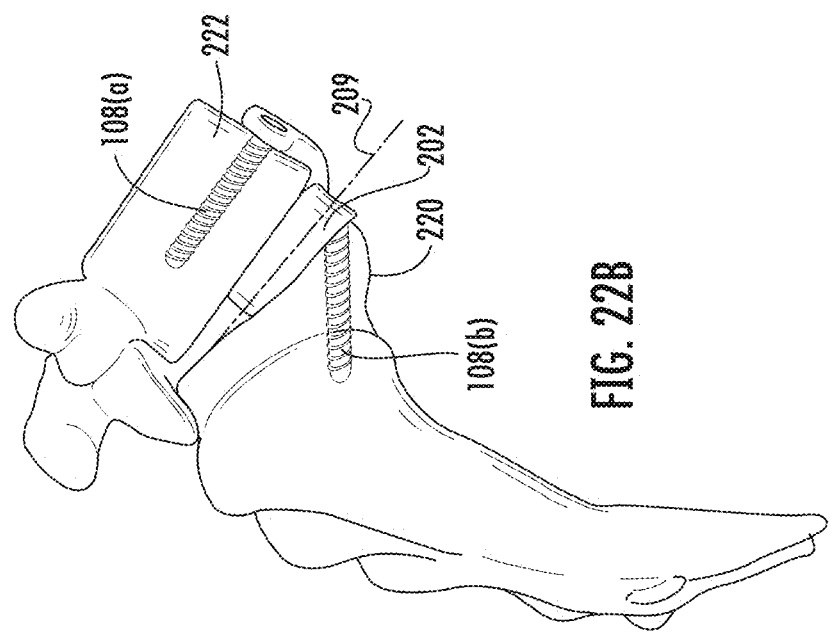
FIGS. 22A-22C illustrate views of another embodiment of a spinal implant of the present disclosure.
Figure 22A:
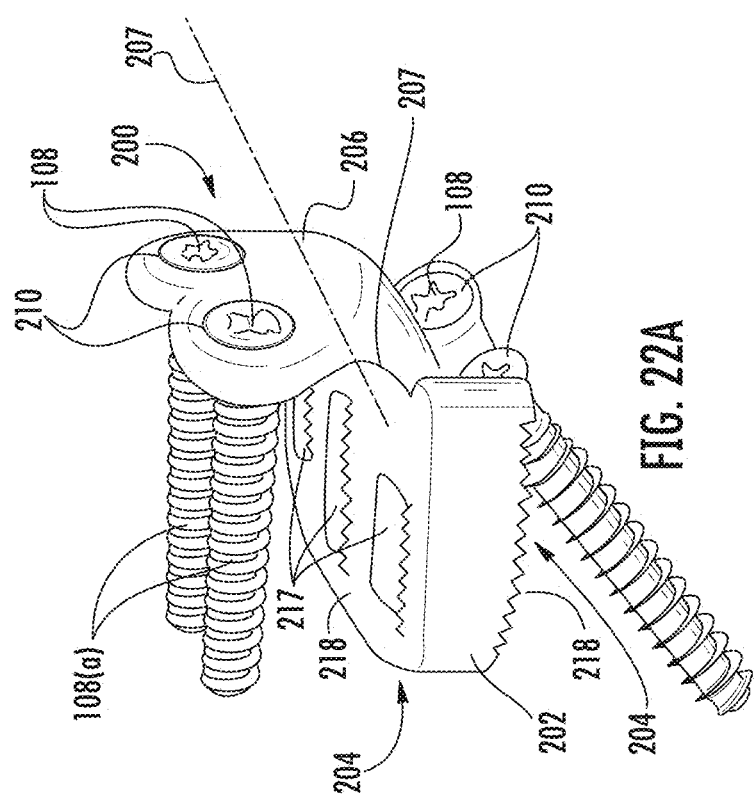
Figure 22C:
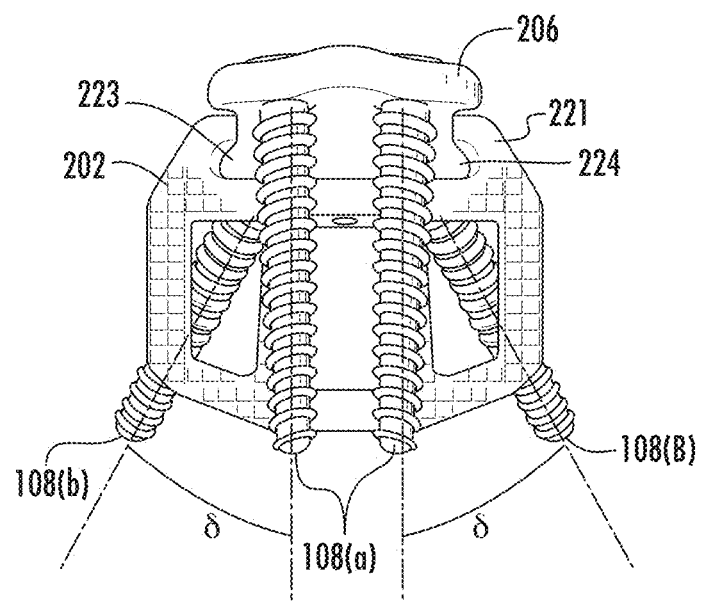

FIGS. 22A-22C illustrate views of another embodiment of a spinal implant 100 of the present disclosure. The spinal implant 200 may be anteriorly inserted into an intervertebral space between two vertebral bodies 222 and 220. For example, the spinal implant 200 may be used for L5-S1 and impart stability to a lytic spondylolisthesis. The spinal implant 200 includes an intervertebral spacer body 202. The intervertebral spacer body 102 includes a pair of opposite sides 204. Each opposite side 204 optionally has pyramid-shaped teeth 218 that are provided to frictionally engage top and bottom surfaces of a vertebral body. The spinal implant 200 also includes a plate 206. The plate 206 has a width of 20 mm to 40 mm and a height of 10 mm to 50 mm. The plate 206 is comprised of a front surface and a rear surface, and may be contoured to optimally engage the vertebral bodies 222 and 220. The plate 206 may include at least two upper boreholes 210 and at least two lower boreholes 210, respectively, asymmetrically positioned about a centerline 207.

As shown in FIG. 22B, the upper screws 108(*a*) and the lower screws 108(*b*) may diverge at an asymmetric angle from a midline 209 of the implant 200. The screws 108 attach the plate 206 to the vertebral bodies (e.g., L5 and S1), between which the intervertebral spacer body 202 may be inserted. The plate 206 is shaped such that the insertion angles of the screws 108 are such that a surgeon may use a straight screwdriver to the insert the screws 108 into the boreholes 210 of the plate 206. The plate 206 provides for ease of insertion and biomechanical integrity. The plate 206 defines a region to mate with the intervertebral spacer body 202. A portion of the rear surface of the plate 206 is adapted to contact a wall of the vertebral body (e.g., body 222).

With reference to FIG. 2C, the spacer body 202 includes a flange 221 and defines a recess 223 that is adapted to engage a coupling 224 of the plate 206. The engagement of the flange 221 and the coupling 224 prevents lateral and rotational movement of the plate 206 with respect to the intervertebral spacer body 202. A screw (not shown) may be inserted into a central hole of the plate 206 to secure the plate 206 to the spacer body 202. The lower screws 108(*b*) may from an angle δ with respect to longitudinal axis of the implant 200. The angle δ may be approximately 20°. The divergent angles of the lower screws 108(*b*) increases the stability of the implant 200. In general, the top set of screws may be parallel and bottom set may be at an angle such that in multiple levels, the bottom (diverging) set of screws do not interfere with the top (parallel) set of screws. The angle δ may be fixed by the aforementioned engagement of the locking threads within the boreholes with the complementary locking threads of the screw heads. The spacer body 202 may have a length to width ratio of approximately between 0.3 and 0.5 when used for, e.g., anterior procedures.

Many modifications and other embodiments of the disclosure set forth herein will come to mind to one skilled in the art to which this disclosure pertains having the benefit of the teachings presented in the foregoing description. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A spinal implant for lateral insertion into an invertebral disc space between a superior and inferior vertebral body, the spinal implant comprising:

a spacer body having a proximal base portion, a distal end, a first side wall and an opposing second side wall; and a plate coupled to the spacer body, the plate having a first side, a second side, a front surface, a rear surface defining a curved face extending away from a top edge of the plate towards the distal end of the spacer body, the plate forming a posterior upper borehole, an anterior upper borehole, a posterior lower borehole and an anterior lower borehole, the lower boreholes positioned about a lateral center plane of the plate from the upper boreholes, the upper boreholes and the lower boreholes adapted to each receive a bone screw to secure the spinal implant within the invertebral disc space, wherein the first side of the plate and the first side wall of the spacer body are sized and configured for location at a posterior position with respect to the invertebral disc space and the second side of the plate and the second side wall of the spacer body are sized and configured for location at an anterior position with respect to the invertebral disc space, wherein the posterior upper and lower boreholes are formed proximate to the first side, and the anterior upper and lower boreholes are formed proximate to the second side, the posterior and anterior upper boreholes positioned opposite each other about a vertical center plane of the plate, wherein a central axis of the anterior upper borehole extends in a predetermined direction transverse to the vertical center plane of the plate towards the first side wall of the spacer body, wherein the curved face defines a first curvature extending between a central vertical axis of the plate and the first side and defining a second curvature extending between the central vertical axis and the second side such that the entire first curvature is asymmetric with the second curvature, wherein the spacer body includes guide grooves aligned with each of the boreholes, the guide grooves formed as arcuate surfaces recessed in and extending along a top and bottom surface of the spacer body, a centerline of each of the arcuate surfaces extending towards the distal end of the spacer body, and a portion of a side edge of each of the guide grooves aligns with one of the first side wall or the second side wall.

2. The spinal implant of claim 1, wherein a central axis of the posterior upper borehole extends in a predetermined direction transverse to the vertical center plane of the plate towards the second side wall of the spacer body.

3. The spinal implant of claim 1, wherein a central axis of the anterior lower borehole extends in a predetermined direction transverse to the vertical center plane of the plate towards the first side wall of the spacer body.

4. The spinal implant of claim 1, wherein the posterior and anterior lower boreholes are positioned opposite each other about the vertical center plane of the plate,
   wherein a central axis of the anterior lower borehole extends a predetermined direction transverse to the vertical center plane of the plate towards the first side wall of the spacer body.

5. The spinal implant of claim 4, wherein a central axis of the posterior lower borehole extends in a predetermined direction generally parallel to the vertical center plane of the plate.

6. The spinal implant of claim 4, wherein the central axes of both the anterior upper borehole and the anterior lower borehole are each formed at an approximately 3° angle with respect to the vertical center plane of the plate.

7. The spinal implant of claim 4, wherein a central axis of the posterior upper borehole and a central axis of the posterior lower borehole each extend in a predetermined direction transverse to the vertical center plane of the plate towards the second side wall of the spacer body.

8. The spinal implant of claim 7, wherein the central axes of each of the posterior upper borehole and the posterior lower bore holes are formed at an approximately 1° angle with respect to the vertical center plane of the plate,
   wherein the central axes of each of the anterior upper borehole and the anterior lower borehole are formed at an approximately 3° angle with respect to the vertical center plane of the plate.

9. The spinal implant of claim 1, wherein a central axis of at least one of the anterior and posterior upper boreholes and a central axis of the anterior lower borehole diverge at symmetric angles about the lateral center plane of the plate.

10. The spinal implant of claim 9, wherein the central axis of the at least one of the anterior and posterior upper borehole is formed at an approximately 5° to 20° angle with respect to the lateral center plane of the plate,
    wherein the central axis of the anterior lower borehole is formed at an approximately 5° to 20° angle with respect to the lateral center plane of the plate.

11. The spinal implant of claim 9, wherein the central axis of at least one of the anterior and posterior upper boreholes is formed at an angle between approximately 10° and 30° with respect to the lateral center plane of the plate,
    wherein the central axis of the anterior lower borehole is formed at an angle between approximately 10° and 30° with respect to the lateral center plane of the plate.

12. The spinal implant of claim 1, wherein a central axis of at least one of the anterior and posterior upper boreholes and a central axis of the anterior lower borehole diverge at asymmetric angles about the lateral center plane of the plate.

13. The spinal implant of claim 12, wherein the central axis of the at least one of the anterior and posterior upper borehole is formed at an angle between approximately 0° to 10° with respect to the lateral center plane of the plate,
    wherein the central axis of the anterior lower borehole is formed at an angle between approximately 10° and 30° with respect to the lateral center plane of the plate.

14. The spinal implant of claim 12, wherein the central axis of the at least one of the anterior and posterior upper borehole is formed at an angle between approximately 5° to 20° angle with respect to the lateral center plane of the plate,
    wherein the central axis of the anterior lower borehole is formed at an angle between approximately 5° to 20° with respect to the lateral center plane of the plate.

15. The spinal implant of claim 14, wherein the central axis of the at least one of the anterior and posterior upper borehole is formed at approximately a 20° angle with respect to the lateral center plane of the plate and the central axis of the anterior lower borehole is formed at approximately a 5° angle with respect to the lateral center plane of the plate.

16. The spinal implant of claim 1, wherein the centerlines of each of the guide grooves is aligned with a corresponding centerline of each of the boreholes.

17. The spinal implant of claim 1, wherein the arcuate surface of each of the guide groove defines a cylindrically-shaped recess having a diameter extending along a length of the guide groove.

18. The spinal implant of claim 1, wherein the portion of the side edge of each of the guide grooves is provided in the proximal base portion of the spacer body,
    wherein a width of the proximal base portion is less than a width of a main body portion, the width of the proximal base portion and the main body portion measured between the first and second side walls,
    wherein the main body portion extends between the proximal base portion and the distal end.

19. A spinal implant for lateral insertion into an invertebral disc space between a superior and inferior vertebral body, the spinal implant comprising:
   a spacer body having a proximal base portion, a distal end, a first side wall and an opposing second side wall; and
   a plate coupled to the spacer body, the plate having a first side sized and configured for location at a posterior position with respect to the invertebral disc space, a second side sized and configured for location at an anterior position with respect to the invertebral disc space, a front surface, a rear surface defining a curved face extending away from a top edge of the plate towards the distal end of the spacer body, the plate forming posterior and anterior upper boreholes and posterior and anterior lower boreholes respectively positioned about a lateral center plane of the plate, each of the boreholes adapted to each receive a bone screw to secure the spinal implant within the invertebral disc space,
   wherein the curved face defines a first curvature extending between a central vertical axis of the plate and the first side and defining a second curvature extending between the central vertical axis and the second side such that the entire first curvature is asymmetric with the second curvature,
   wherein the posterior upper and lower boreholes are formed proximate the first side of the plate and the anterior upper and lower boreholes are formed proximate the second side of the plate,
   wherein the upper and lower boreholes have an asymmetric configuration relative to a vertical center plane of the plate, a central axis of each of the anterior upper and lower boreholes is configured to extend in a predetermined direction transverse to the vertical center plane of the plate towards the first side wall of the spacer body and a posterior side of the invertebral disc space, a central axis of each of the posterior upper and lower boreholes extends in a predetermined direction generally parallel to the vertical center plane of the plate.

20. The spinal implant of claim 19, wherein the central axis of the anterior upper borehole is formed at an approximately 3° angle with respect to the vertical center plane of the plate.

* * * * *